(12) United States Patent
Hantash et al.

(10) Patent No.: US 9,320,698 B2
(45) Date of Patent: Apr. 26, 2016

(54) PEPTIDE TYROSINASE INHIBITORS AND USES THEREOF

(75) Inventors: Basil M. Hantash, East Palo Alto, CA (US); Anan Abu Ubeid, San Jose, CA (US)

(73) Assignee: Escape Therapeutics, Inc., San Jose, CA (US)

( * ) Notice: Subject to any disclaimer, the term of this patent is extended or adjusted under 35 U.S.C. 154(b) by 0 days.

(21) Appl. No.: 14/117,012

(22) PCT Filed: May 10, 2012

(86) PCT No.: PCT/US2012/037332
§ 371 (c)(1),
(2), (4) Date: Jan. 22, 2014

(87) PCT Pub. No.: WO2012/154959
PCT Pub. Date: Nov. 15, 2012

(65) Prior Publication Data
US 2015/0118286 A1 Apr. 30, 2015

Related U.S. Application Data

(60) Provisional application No. 61/484,896, filed on May 11, 2011.

(51) Int. Cl.
| | | |
|---|---|---|
| *A61K 8/64* | (2006.01) | |
| *C07K 7/06* | (2006.01) | |
| *C12N 9/02* | (2006.01) | |
| *A61Q 19/02* | (2006.01) | |
| *A61K 8/14* | (2006.01) | |
| *C07K 5/11* | (2006.01) | |
| *A61Q 19/00* | (2006.01) | |
| *A61K 38/00* | (2006.01) | |

(52) U.S. Cl.
CPC ... *A61K 8/64* (2013.01); *A61K 8/14* (2013.01); *A61Q 19/007* (2013.01); *A61Q 19/02* (2013.01); *C07K 5/1019* (2013.01); *C07K 7/06* (2013.01); *C12N 9/0071* (2013.01); *C12Y 114/18001* (2013.01); *A61K 38/00* (2013.01); *A61K 2800/30* (2013.01); *A61K 2800/782* (2013.01); *A61K 2800/81* (2013.01); *A61K 2800/82* (2013.01)

(58) Field of Classification Search
CPC ....................................................... A61K 8/64
See application file for complete search history.

(56) References Cited

U.S. PATENT DOCUMENTS 5,641,861 A * 6/1997 Dooley et al. ................. 530/329

FOREIGN PATENT DOCUMENTS

| WO | WO 01/66147 | * | 9/2001 | ............. A61K 47/48 |
| WO | WO 2009/117524 | * | 9/2009 | ............. C40B 30/04 |

* cited by examiner

*Primary Examiner* — Amber D Steele
(74) *Attorney, Agent, or Firm* — Aka Chan LLP

(57) ABSTRACT

Disclosed are peptides that inhibit the enzymatic activity of tyrosinase, as well as formulations and methods for their use in the reduction of skin pigmentation, and methods of administering the inhibitory pep tides in a topical formulation. Preferred octapeptide sequences are internally rich in tryptophan and/or tyrosine or arginine. The present invention is further directed to kits and compositions containing the present peptides, and methods of treatment of conditions involving expression of tyrosinase, in which the present peptides are administered topically for the treatment of conditions involving melanocyte activity in the skin.

24 Claims, 8 Drawing Sheets

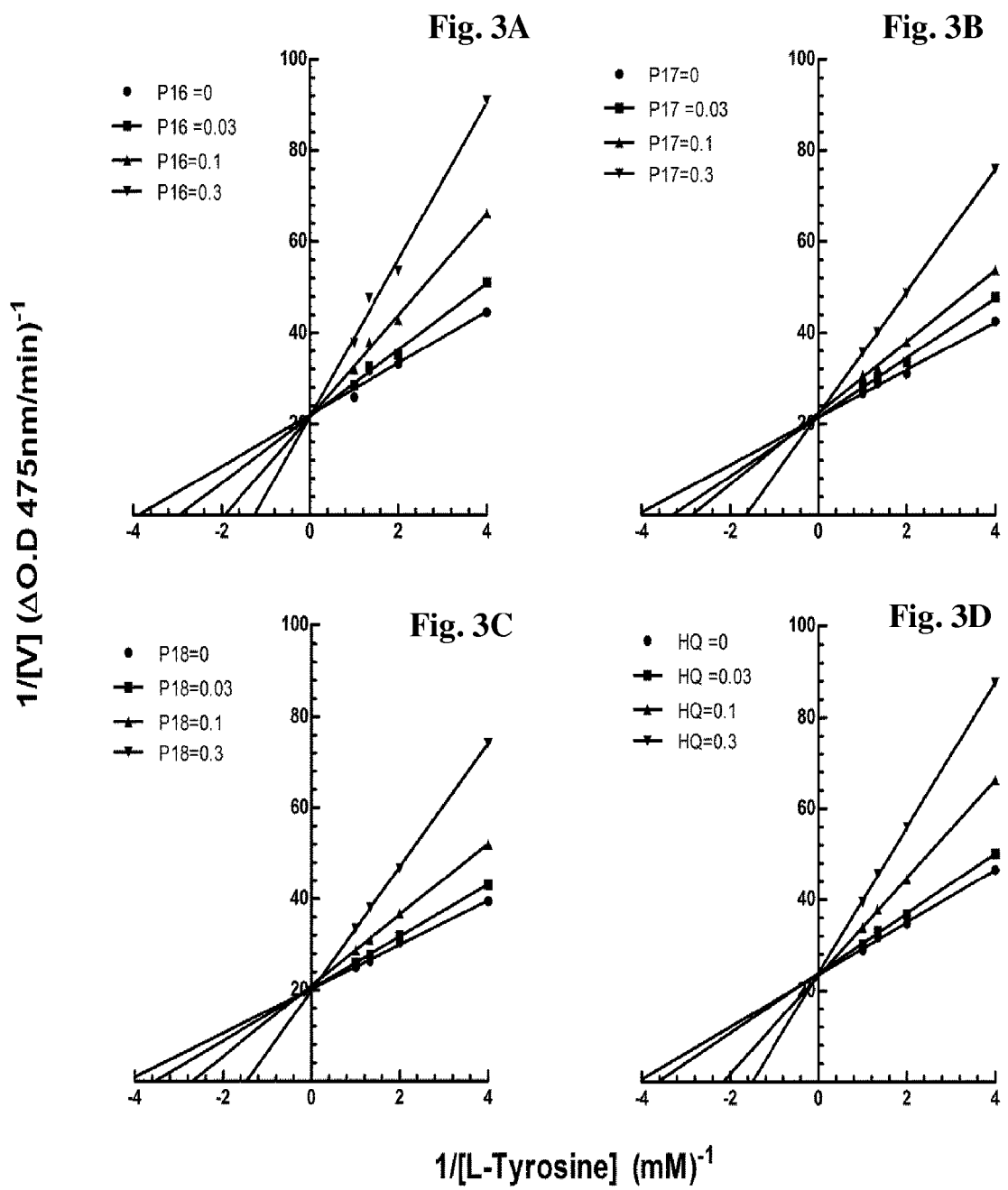

Toxicity (% control)

[mM]

PEPTIDE TYROSINASE INHIBITORS AND USES THEREOF

This application is a U.S. national phase application under 35 U.S.C. section 371 (f) of international application PCT/US 2012/037332, filed May 10, 2012, which claims priority from U.S. Provisional Patent Application 61/484,896 filed on May 11, 2011, which are hereby incorporated by reference in its entirety.

STATEMENT OF GOVERNMENTAL SUPPORT

None.

REFERENCE TO SEQUENCE LISTING, COMPUTER PROGRAM, OR COMPACT DISK

Applicants submit herewith a sequence listing in an ASCII text file (5712_01_PCT_Seq_Listing), as provided in EFS Legal Framework Notice 20 May 2010, part I-I-1. The file was created May 1, 2012 and contains 3,557 bytes. Applicants incorporate the contents of the sequence listing by reference in its entirety.

BACKGROUND OF THE INVENTION

1. Field of the Invention

The present invention relates to the field of tyrosinase inhibitors and to methods and compositions of treatment involving inhibition of this enzyme.

2. Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

The present invention relates to novel biological agents, specifically oligopeptides that reduce the enzymatic activity of tyrosinase. These agents have use as research and development tools in basic science investigation, in diagnostic applications, as cosmeceuticals for the treatment of pigmentary disorders including skin conditions characterized by hyperpigmentation, and as therapeutics for the treatment of pathological conditions that rely on tyrosinase enzyme activity to promote their tumorigenicity or other adverse effects.

Melanin plays an important role in protecting the human body from the harmful effects of ultraviolet rays. Melanin is also an important factor in medical science and cosmetology. It is known that melanin is formed or synthesized in skin tissues. Excessive amounts of melanin darken the skin, and the nonuniform distribution of melanin causes chloasma and ephelis, both of which are skin disorders.

Melanin is a photoprotective biopolymer synthesized by melanocytes in discrete organelles known as melanosomes. Once filled with melanin, epidermal melanosomes are transferred to keratinocytes, where they form a supranuclear cap to protect DNA against ultraviolet irradiation. The type, amount, and distribution pattern within surrounding keratinocytes help determine skin color. Melanin forms through a series of oxidative reactions involving the amino acid tyrosine and the enzyme tyrosinase. Since its discovery in 1896 by Bourquelot and Bertrand, the enzyme tyrosinase has been extensively studied and its rate limiting role in the melanin biosynthetic pathway has since been elucidated through the work of Raper et al (Biochem J., 1923, 17: 454-469), Mason H S (J. Biol. Chem., 1948, 172: 83-99), Cooksey et al (J. Biol. Chem., 1997, 272: 26226-26235) and Schallreuter et al (Exp. Dermatol., 2008, 17: 395-404).

Tyrosinase is a melanocyte-specific, multi-functional, glycosylated, copper containing oxidase with a molecular weight of approximately 60-70 kDa in mammals. Defects in the enzyme's activity lead to albinism in humans. It is believed that racial differences in skin color may primarily be due to differences in tyrosinase activity. Melanocytes derived from African skin demonstrate up to ten times more activity and melanin production than melanocytes from Caucasian skin. However, this is not due to a greater abundance of tyrosinase, as both skin types have been shown to contain a similar density of tyrosinase molecules. The first two steps in the melanogenic pathway are hydroxylation of L-tyrosine to 3-4-dihydroxyphenylalanine (L-dopa) and the oxidation of L-dopa to o-dopaquinone, a highly reactive compound that spontaneously polymerizes to form melanin.

The most common pigmentary disorders for which patients seek treatment are melasma and post-inflammatory hyperpigmentation (Lynde, C. B., Kraft, J. N., and Lynde, C. W. (2006) Skin Therapy Lett 11, 1-6). These conditions may have a major impact on a person's psychological and social well-being, contributing to lower productivity, social functioning, and self-esteem (Finlay, A. Y. (1997) Br J Dermatol 136, 305-314) as well as a negative impact on the person's health-related quality of life (Balkrishnan, R., McMichael, A. J., Camacho, F. T., Saltzberg, F., Housman, T. S., Grummer, S., Feldman, S. R., and Chren, M. M. (2003) Br J Dermatol 149, 572-577; Taylor, A., Pawaskar, M., Taylor, S. L., Balkrishnan, R., and Feldman, S. R. (2008) J Cosmet Dermatol 7, 164-168). Thus, pharmacological agents that can reduce hyperpigmentation are of great interest clinically (Solano, F., Briganti, S., Picardo, M., and Ghanem, G. (2006) Pigment Cell Res 19, 550-571), and include hydroquinone (dihydroxybenzene; HQ) (Jimbow, K., Obata, H., Pathak, M. A., and Fitzpatrick, T. B. (1974) J Invest Dermatol 62, 436-449), arbutin (Maeda, K., and Fukuda, M. (1996) J Pharmacol Exp Ther 276, 765-769), kojic acid (Cabanes, J., Chazarra, S., and Garcia-Carmona, F. (1994) J Pharm Pharmacol 46, 982-985), vitamin C (Kojima, S., Yamaguchi, H., Morita, K., and Ueno, Y. (1995) Biol Pharm Bull 18, 1076-1080), retinol (Pathak, M. A., Fitzpatrick, T. B., and Kraus, E. W. (1986) J Am Acad Dermatol 15, 894-899), azelaic acid (Schallreuter, K. U., and Wood, J. W. (1990) Arch Dermatol Res 282, 168-171), as well as a number of botanical compounds (Hwang, J. H., and Lee, B. M. (2007) J Toxicol Environ Health A 70, 393-407).

To date, the mainstay treatment for hyper-pigmentation has been hydroquinone (HQ) at a concentration of 2-4% (Ennes, S., et al. Journal of Dermatological Treatment, 2000, vol 11, pages 173-179). In addition to tyrosinase inhibition, HQ has been shown to degrade melanosomes and induce apoptosis in melanocytes (Arck, P. C., et al. FASEB Journal, 2006, vol 20, pages 1567-1569; Inayat-Husain, S. H., et al. Chem. Res. Toxicol., 2005, vol 18, pages 420-427; and Penney, K. B., et al. J. Invest. Dermatol, 1984, vol 82, pages 308-310). It was also found that HQ achieves its hypopigmenting effects through depletion of glutathione, leading to the generation of reactive oxygen species and subsequent oxidative damage of membrane lipids and proteins (Briganti, S., et al., Pigment Cell Research, 2003, vol 16, pages 101-110). HQ's pleiotropic effects are complicated by a number of adverse reactions including contact dermatitis, irritation, transient erythema, burning, prickling sensation, leukoderma, chestnut spots on the nails, hypochromia and ochronosis (Engasser, P. G., J. Am. Acad. Dermatol., 1984, vol 10, pages 1072-1073; Romaguera, C., et al. Contact Dermatitis, 1985, vol 12, page 183). Moreover, HQ is potentially mutagenic to mammalian cells. HQ and its derivative arbutin are both catabolized to benzene metabolites with the potential for bone marrow toxicity (Curto, E. V., et al. Biochem. Pharmacol., 1999, vol 57, pages 663-672; Zhou, H., et al. Mol. Pharmacol., 2009, vol 76, pages 579-587).

Hydroquinone (HQ) has been used since the 1950's in commercially available over-the-counter skin lightener products and since the 1960's as a commercially available medical product. It is also used in cosmetic products such as hair dyes and products for coating fingernails. However, beginning in 2001, HQ is no longer authorized for use in cosmetic skin lightening formulations in European Union countries, although products containing arbutin, an analogue of HQ, and botanicals, including plants that naturally contain HQ and arbutin, continue to remain available in European countries See also, Matsubayashi et al., "Pharmaceutical and clinical assessment of hydroquinone ointment prepared by extemporaneous nonsterile compounding," Biol Pharm Bull. 2002 January; 25(1):92-6. As disclosed there, ointments of the skin depigmentation agent HQ have been prepared by extemporaneous nonsterile compounding in Japan by imitating skin lightening creams commercially available in the U.S.A. and European Union. However, various problems have been observed including chromatic aberration of HQ ointments, relatively large variability of efficacy, and undesirable side effects although they were mild. HQ has a published IC50 of about 700 μM.

Therapies containing HQ have been outlawed in Asian countries, making the standard HQ treatment inaccessible to a large number of people suffering from this condition. In fact, the United States FDA has issued a notice indicating that it may too ban the use of HQ domestically. Furthermore, HQ has been associated with visceral malignancy and long-term topical delivery may be a potentially harmful therapeutic option. HQ in the best of circumstances leads to only a partial alleviation of hyperpigmentation. Some cosmeceutical formulations (i.e. compositions) have included other active ingredients such as kojic acid, arbutin, and vitamin C but efficacy has thus far been disappointing due to problems with chemical instability or inability to deliver the active to the appropriate layer of skin. HQ and its derivative arbutin are both catabolized to benzene metabolites with the potential for bone marrow toxicity (Zhou, H., Kepa, J. K., Siegel, D., Miura, S., Hiraki, Y., and Ross, D. (2009) Mol Pharmacol 76, 579-587). Similarly, kojic acid, fungally derived HQ derivative, has been shown to promote thyroid and liver carcinogenicity in rodent models (Fujimoto, N., Onodera, H., Mitsumori, K., Tamura, T., Maruyama, S., and Ito, A. (1999) Carcinogenesis 20, 1567-1571), leading to its ban in Switzerland. Although higher concentrations have been utilized, patients often discontinue treatment due to skin irritation. This led to the addition of topical steroids in order to reduce irritation from the active ingredients such as retin A and HQ. Since melasma and other hyperpigmentary disorders often take months to years to treat, use of topical steroids on the face at the strength required to combat irritant effects of active ingredients is not possible without causing topical steroid-induced side effects. When medium or greater potency topical steroids are used on the face for more than several weeks consecutively, skin atrophy, fragility and telengiectasia commonly occur. This side effect profile is unacceptable, especially in areas such as the face.

Infrared lasers have been used with some success. They generally are more effective for conditions that localize pigment to the deeper skin areas such as the dermis. In order to effectively treat the epidermis, an ablative treatment is usually employed. This therapy is associated with significant downtime for the patient, including creation of second-degree burn or erosion leaving the patient susceptible to infection. In addition, laser therapy is an expensive treatment option that many patients cannot afford. In extreme cases, depigmentation of the skin has been elected when bleaching agents have been unsuccessful. Numerous pathological conditions can lead to the deposition of pigment into the skin aberrantly. For example, it is well known that hormonal imbalance can cause facial and extremity hyperpigmentation, most frequently observed in women during or following pregnancy. Often times, this hyperpigmentation becomes aesthetically disfiguring, leading to problems with self-esteem and embarrassment in social situations. Melasma often times affects individuals with Fitzpatrick type IV-VI skin. This constitutes a significant portion of the worldwide population.

A large number of individuals with Fitzpatrick type IV to VI skin are of Asian descent.

According to the Fitzpatrick skin type scale, based on a test of appearance and skin reaction to sun exposure, individuals are generally categorized as follows:

Type I: Very fair skin tone, blond or redhead,
Type II: Light skin tone, will tan, but usually burns.
Type III: White to olive skin tone, sometimes burns.
Type IV: Medium brown skin tone, rarely burns.
Type V: Dark brown skin tone, very rarely burns.
Type VI: Black skin tone, very dark eyes, burn resistant.

In addition to melasma, hyperpigmentation of aesthetically sensitive locations such as the face may take place after inflammation due to disorders such as acne or rosacea, amongst others. These conditions may also lead to significant psychological discomfort. In the United States, $13 billion are spent on cosmeceuticals each year. With the anticipated ban of HQ in the US market, in conjunction with the continued stability (vitamin C) or delivery (arbutin, kojic acid, etc) problems of other non-pharmacological agents currently on the market, oligopeptide inhibitors may provide a solution to this large unmet need.

Specific Patents and Publications

Scot et al., "Production of cyclic peptides and proteins in vivo," Proc. Nat. Acad. Sci. Vol. 96, Issue 24, 13638-13643, Nov. 23, 1999, discloses the production of the cyclic, eight-amino acid tyrosinase inhibitor pseudostellarin F in bacteria.

Verma et al., "Modulation of agonist binding to human dopamine receptor subtypes by L-prolyl-L-leucyl-glycinamide and a peptidomimetic analog," J Pharmacol Exp Ther. 2005 December; 315(3):1228-36. Epub 2005 Aug. 26, discloses the role of the hypothalamic tripeptide L-prolyl-L-leucyl-glycinamide (PLG) and its conformationally constrained analog 3(R)-[(2(S)-pyrrolidinylcarbonyl) amino]-2-oxo-1-pyrrolidineacetamide (PAOPA) in modulating agonist binding to human dopamine (DA) receptor subtypes.

U.S. Pat. No. 6,165,982 to Yamada, et al., issued Dec. 26, 2000 entitled "Use of sericin as antioxidants and tyrosinase inhibitors," discloses a composition useful as an antioxidant or an inhibitor for tyrosinase activity which comprises as an active ingredient a sufficient amount of sericin to exert an antioxidizing ability. Sericin is a high molecular weight, natural, soluble glycoprotein constituent of silk. Sericin binds to the keratin of skin and hair, forming a protective film.

U.S. Pat. No. 5,126,327 to Takeuchi, et al., issued Jun. 30, 1992, entitled "Melanocyte-stimulating hormone inhibitor and external preparation containing the same," discloses a melanocyte-stimulating hormone inhibitor which has certain amino acid sequences, an acyl group having 1 to 12 carbon atoms, an amino acid residue, or acylated derivative thereof having 1 to 12 carbon atoms, peptide residue having 2 to 40 amino acid residues or acylated derivative thereof.

U.S. Pat. No. 7,025,957 to Arquette, issued Apr. 11, 2006, entitled "Composition and method to whiten skin," discloses a composition effective as a skin whitening agent. The composition includes Simmondsin, which is a glycoside extracted from jojoba meal (*Simmondsia chinensis*). In certain embodiments, the composition comprises an extract of jojoba (*Simmondsia chinensis*). The composition is administered by topically applying to an individual a formulation in an amount effective to whiten skin, where that composition comprises a jojoba extract.

U.S. Pat. No. 7,083,781 to Fotinos, et al., issued Aug. 1, 2006, entitled "Film forming polymers, methods of use, and devices and applications thereof," discloses compositions and methods for delivering active agents to the skin of a subject, including a polymer, an active ingredient and a solvent, the compositions being capable of delivery by rolling, spreading, aerosol or in droplets and of forming a film in contact with the skin. A cosmetic active agent known in the art may be incorporated in the film forming compositions for improving skin appearance. Anti-hyperpigmentation agents typically used for counterbalancing this condition can include tyrosinase inhibitors such as peptide mixtures and plant extracts, fermentation products, and antioxidants such as hydroquinone, kojic acid, ascorbic acid derivatives, synthetic or natural derivatives of hydroquinone and hydroquinone precursors. In preferred embodiments of the invention, anti-hyper pigmentation agents are Melawhite of Pentharm Ltd., Basel, Switzerland; Biowhite™ of Coletica, France; Etioline of Sederma, France; Arbossa of Kelesima, Italy; Gatuline whitening of Gattefosse, France; Ascorbocilan C of Exsymol, Monaco; and Kojic acid of Alps Pharm., Japan.

U.S. Pat. No. 7,125,572 to Lee, issued Oct. 24, 2006, entitled "Tyrosinase inhibitor extract," discloses a tyrosinase inhibitor extract from lemon peels. The tyrosinase inhibitor provides advantageous skin whitening effects. According to the invention, the tyrosinase inhibitor extract of the invention has a main absorbance at 280 nm. This indicates that the tyrosinase inhibitor extract contains a protein or peptide. It is believed that the protein or peptide is the main active component for inhibiting tyrosinase. The other components of the extract may provide additional effects such as anti-aging and anti-oxidation. The tyrosinase inhibitor extract can be prepared to be in various forms, including lotions, emulsions, creams, ointments, sticks, solutions, packs, and gel. The tyrosinase inhibitor extract may be admixed with any ingredients ordinarily used in cosmetics, such as oily substances, humectants, thickeners, preservatives, emulsifiers, medical ingredients, perfumes, emulsification stabilizers and the like.

BRIEF SUMMARY OF THE INVENTION

The following brief summary is not intended to include all features and aspects of the present invention, nor does it imply that the invention must include all features and aspects discussed in this summary.

The present invention concerns certain peptide sequences exemplified as:

```
                                           SEQ ID NO: 1
>1 ("P16" peptide)
RRWWRRYY;

SEQ ID NO: 2
>2 ("P17" peptide)
RRRYWYYR;
and

SEQ ID NO: 3
>3 ("P18" peptide)
RRYWYWRR
```

The present invention is further directed to kits and compositions containing the present peptides, and methods of treatment of conditions involving expression of tyrosinase, in which the present peptides are administered topically for the treatment of conditions involving melanocyte activity in the skin. Other formulations are useful in treating tyrosinase activity in other regions of the body and may be administered internally.

The peptides may be considered in tabular form with columns for each position one through eight, showing P16-P18 and possible variations as follows:

| SEQ ID | 1 | 2 | 3 | 4 | 5 | 6 | 7 | 8 |
|---|---|---|---|---|---|---|---|---|
| 1-P16 | R | R | W | W | R | R | Y | Y |
| 2-P17 | R | R | R | Y | W | Y | Y | R |
| 3-P18 | R | R | Y | W | Y | W | R | R |
| *4-P13* | *R* | *R* | *V* | *A* | *L* | | | |
| *5-P14* | *R* | *R* | *F* | *V* | *I* | *L* | | |
| *6-P15* | *R* | *R* | *F* | *V* | *C* | *C* | | |
| 7-P16a | R | R | W | W | R | R | | |
| 8-P16b | R | W | W | R | | | | |
| 9-P16c | R | W | W | R | R | Y | | |
| 10-P17a | R | R | Y | W | Y | Y | | |
| 11-P17b | R | R | Y | W | Y | Y | R | |
| 12-P18a | R | R | R | Y | W | Y | W | |
| 13-P18b | R | Y | W | Y | W | R | | |
| 14-P18c | Y | W | Y | W | R | R | | |

The underlined peptides P13-P15 had strong binding but weak inhibition, as described below. It is therefore considered desirable to have an aromatic or charged residue in the central part of the peptide. Thus, in certain aspects, the present invention is directed to a purified peptide selected from the group comprising P16 (SEQ ID NO: 1), P17 (SEQ ID NO: 2) and P18 (SEQ ID NO: 3), or a fragment or a variant thereof and having an $IC_{50}$ of tyrosinase of less than about 0.5 mM, or less than 0.4 mM, or less than 0.3 mM. In some cases, the peptide will have an $IC_{50}$ of less than about 0.4 mM, or even less. The peptide in effect may be substituted in up to three positions, including deletions, with reference to a specific sequence set forth here, such as SEQ ID NO: 1, 2 or 3. It is also advantageous in some embodiments to have two adjacent charged amino acids. In certain aspects, the invention comprises the use of D-amino acids for some or all of the amino acids. In certain aspects, the peptide comprises aromatic residues W or Y in the 3rd or $4^{th}$ position through the $7^{th}$ or $8^{th}$ position of an octapeptide. If the peptide is shorter, the aromatic amino acid residues will correspondingly be internal residues, as shown in the Table above. Octapeptides are preferred in certain embodiments. The peptides may be linked to a modulating group, as defined below, such as palmitic acid or ester.

In certain aspects, the present invention comprises a topical formulation useful in skin whitening. The formulation is dermatologically acceptable, i.e. made from ingredients suitable for application to the skin. The formulation may comprise standard carrier material, as well as in certain cases, a secondary treatment agent and a peptide essentially identical to a sequence selected from the group consisting of P16 (SEQ ID NO: 1), P17 (SEQ ID NO: 2) and P18 (SEQ ID NO: 3) or peptide variants thereof which have substantial sequence identity to SEQ ID NOs: 1, 2 or 3. In certain embodiments, the formulations may be adapted for potential over the counter use, or for prescription use. For over the counter use, one may employ a formulation wherein the peptide is at a concentration less than about two times the $IC_{50}$ concentration. For pharmaceutical use, one may the peptide may be at a concentration of two to 100 times the $IC_{50}$ concentration.

The present peptides are in certain aspects superior to HQ, and may be formulated to be substantially free of HQ. The present peptides are also substantially less toxic than HQ. In certain formulations, different peptides may be combined, with different sequences, different attached groups, and so forth. The carrier may include a material selected from: hydrating formulations, antioxidant formulations, and free radical scavengers.

In certain formulations, the present peptides will have improved skin uptake by being formulated in liposomes.

In certain aspects, the present invention comprises methods of skin treatment, involving skin lightening (whitening). This aspect includes a method for treatment of skin comprising administering to the skin a peptide essentially identical to one of: (P16 (SEQ ID NO: 1), P17 (SEQ ID NO: 2) and P18 (SEQ ID NO: 3) wherein said administering of the peptide inhibits tyrosinase sufficiently to lighten skin pigmentation. The administering may comprise administering a topical preparation, as referred to above, and may further comprise a secondary treatment product.

The present methods of treatment also include carrying out the skin whitening with further assistance from a microdermabrasion process. The administering may be simultaneous with the microdermabrasion process. The administering is in conjunction with a radiation process. Such processes may be used to increase skin permeability. Furthermore, the administering may be in conjunction with a physical treatment carried out by an abrading device a microneedle, an electroporation device, or an iontophoretic device.

In certain aspects, the present invention comprises a kit for carrying out a skin whitening procedure, comprising a purified peptide having an $IC_{50}$ of tyrosinase of less than about 0.5 mM and selected from the group consisting of: a peptide having and a sequence essentially identical to the sequence of either P16 (SEQ ID NO: 1), P17 (SEQ ID NO: 2) and P18 (SEQ ID NO: 3); a dermatologically acceptable carrier; a secondary treatment product; and directions for use. The kit may be aimed at consumers or physicians, and may include a precombination of the peptide and carrier, such that the formulation is ready to apply, or it may require mixing of the peptide with the carrier.

In certain aspects, the present invention concerns peptides that inhibit tyrosinase, which have a formula according to one of:
(a) $X^1$ R W W R $X^6$ $X^7$ $X^8$ (SEQ ID NO: 15),
(b) $X^1$ $X^2$ R Y W Y Y $X^8$ (SEQ ID NO: 16), and
(c) $X^1$ $X^2$ Y W Y W $X^7$ $X^8$ (SEQ ID NO: 17),
where $X^1$, $X^2$, $X^6$, $X^7$ and $X^8$ are each independently one of R, Y, and missing.

Based on the formulas (a), (b), and (c), the present peptides may have a variety of amino acid residue combinations, as can be seen from the P16-P18 variations listed in the table above. In some embodiments, the peptide sequence may consist of eight amino acids (an "octapeptide"). In other embodiments, the peptide sequence may be shorter than 8 amino acids because of a deletion or multiple deletions. For example, RRWWRR (SEQ ID NO: 7) where the sequence is of formula (a) and $X^1$ is R, $X^6$ is R, and both $X^7$ and $X^8$ are missing. In yet another embodiment, the peptide may have a formula of (a), (b), or (c) wherein $X^1$, $X^2$, $X^6$, $X^7$ and $X^8$ are each Y or R. For example, RRYWYWRR (SEQ ID NO: 3) where the sequence is of formula (c) and $X^1$, $X^2$, $X^7$ and $X^8$ are R.

In other embodiments, an amino acid may have a formula according to formula (a) wherein $X^8$ is Y or missing. For example, RRWWRRYY (SEQ ID NO: 1), which is of formula (a) and where $X^8$ is Y.

BRIEF DESCRIPTION OF THE DRAWINGS

FIGS. 3A, 3B, 3C, and 3D is a set of four Lineweaver-Burk plots of mushroom tyrosinase activity in the presence of octapeptides or HQ. (A) P16, (B) P17, (C) P18, and (D) HQ. The concentration of mushroom tyrosinase [E] was 24 units/ml. [5] was 0.01 mg/ml and up to 5 times the observed $K_m$. [I] ranged from 0 to 0.3 mM. Data were obtained as mean values of 1/V, inverse of the increase of absorbance at wavelength of 475 nm per minute ($\Delta A_{475}$/min) for 5 independent trials. Michaelis Menten constant ($K_m$) and the dissociation constant $K_i$ were derived using nonlinear regression analysis with GraphPad Prism 5.

DETAILED DESCRIPTION OF THE PREFERRED EMBODIMENT

Overview

Figure 1A:
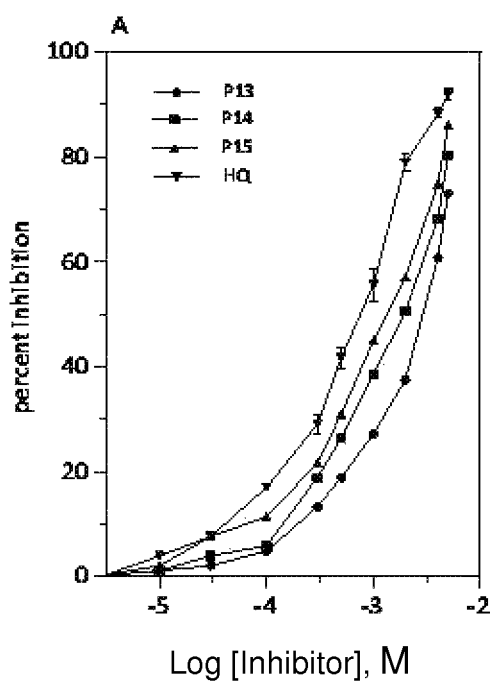
FIGS. 1A and 1B is a pair of graphs showing dose-dependent inhibitory effects of oligopeptides and HQ on mushroom tyrosinase. (A) Percent inhibition curves for P13-15 and HQ. (B) Percent inhibition curves for P16-18 and HQ. Results represent a minimum of 5 independent runs, and are shown as means±S.E.

Described herein are new oligopeptide tyrosinase inhibitors having improved properties such as high potency, short sequence length, low toxicity and enhanced cell penetration. Short peptides of between about 6 and 12 amino acids, preferably 8 amino acids are disclosed and shown to have inhibitory activity against tyrosinase. Short peptides are synthetically designed in certain embodiments using naturally occurring amino acids, and therefore are biologically safe. They can be delivered to melanocytes through a number of mechanisms, including but not limited to liposomes, allowing access to the appropriate skin layer. These peptides do not suffer from oxidation problems, as does the most commonly used ingredient, vitamin C. These peptides do not cause cancer or are not toxic to skin cells, as does hydroquinone, and since they are derived from or consist of naturally occurring amino acids, are easily degraded intracellularly upon inactivation of tyrosinase. They cause skin lightening or whitening by inhibiting the synthesis of melanin.

The present invention is directed in large part to peptides P15, P16, P17, and P18, and variants thereof. Some of these variants include:

In addition, the following peptides were also used:

```
                                              SEQ ID NO: 4
>4 ("P13" PEPTIDE)
RRVAL

SEQ ID NO: 5
>5 ("P14" PEPTIDE)
RRFVLL

SEQ ID NO: 6
>6 ("P15" PEPTIDE)
RRFVCC
```

In addition, variations to the exact sequence may be made such as:

```
                                              SEQ ID NO: 7
>7
RRWWRR

SEQ ID NO: 8
>8
RWWR

SEQ ID NO: 9
>9
RWWRRY

SEQ ID NO: 10
>10
RRYWYY

SEQ ID NO: 11
>11
RYWYYR

SEQ ID NO: 12
>12
RRYWYW

SEQ ID NO: 13
>13
RYWYWR

SEQ ID NO: 14
>14
YWYWRR
```

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The term "tyrosinase" is used herein to refer to monophenol monooxygenase (EC 1.14.18.1; CAS number: 9002-10-2), an enzyme that catalyses the oxidation of phenols (such as tyrosine). It is a copper-containing enzyme present in plant and animal tissues that catalyzes the production of melanin and other pigments from tyrosine by oxidation. All tyrosinases have in common a binuclear type-3 copper center within their active site. Here two copper atoms are each coordinated with three histidine residues. Matoba et al., "Crystallographic evidence that the dinuclear copper center of tyrosinase is flexible during catalysis," *J Biol Chem.*, 2006 Mar. 31; 281(13):8981-90. Epub 2006 Jan. 25, discloses a three-dimensional model of a tyrosinase catalytic center. Human tyrosinase isoform 1 has been chosen as the canonical sequence, but isoform 2 and other single amino acid variants may be considered as human tyrosinase. See, e.g. UniProtKB/Swiss-Prot P14679 (TYRO_HUMAN).

The term "peptide" is used herein in its conventional sense, i.e., a polymer in which the monomers are amino acids and are joined together through amide bonds, alternatively referred to as a polypeptide. When the amino acids are α-amino acids, either the L-optical isomer or the D-optical isomer may be used. Additionally, unnatural amino acids, for example, β-alanine, phenylglycine and homoarginine are also meant to be included. The present peptides are two or more amino acid monomers long and may be up to 20 amino acid monomers long. Standard abbreviations for amino acids are used (as described below). Sequences are given here in standard form, from amino terminus to carboxy terminus.

The term "carrier" refers to compounds commonly used on the formulation of pharmaceutical compounds used to enhance stability, sterility and deliverability of the therapeutic tyrosinase inhibitor. When the peptide delivery system is formulated as a solution or suspension, the delivery system is in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The term "topical" or "topically" is used here in its conventional sense as referring to a spot, which can be in or on any part of the body, including but not limited to the epidermis, any other dermis, or any other body tissue. Topical administration or application means the direct contact of the peptide with tissue, such as skin or membrane, which contains melanin-producing cells. Methods of applying the present topical agents to the skin or mucosa include "non-finite" or liquid or semi-liquid carriers such as gels, lotions, emulsions, creams, plasters, or ointments, or "finite" carriers, non-spreading substances which retain their form, e.g., patches, dressings and bandages. The solvents for the finite and non-finite forms of the active peptides are non-toxic, pharmaceutically acceptable substances, preferably liquids, which do not substantially negatively affect the adhesion properties or solubility of the system. The solvent is preferably a polyhydric alcohol or combination of polyhydric alcohols. The term polyhydric alcohol means any organic polyalcohol and includes dipropylene glycol, propylene glycol, polyethylene glycol, glycerin, butylene glycol, hexylene glycol, polyoxyethylene, polypropylene glycol, sorbitol, ethylene glycol, and the like. Other suitable solvents include fatty acids such as oleic acid, linoleic acid, capric acid and the like, as well as fatty esters or alcohols. Further suitable solvents include other non-toxic, non-volatile solvents commonly used in dermal or transdermal compositions for dissolving peptide-based compositions.

The term "sequence identity" in the context of two polypeptide sequences refers to the residues in the two sequences, which are the same when aligned for maximum correspondence. Optimal alignment of sequences for comparison can be conducted, e.g., by the local homology algorithm of Smith and Waterman, *Adv. Appl. Math.* 2: 482 (1981), by the homology alignment algorithm of Needleman and Wunsch, *J. Mol. Biol.* 48:443 (1970), by the search for similarity method of Pearson and Lipman, *Proc. Natl. Acad. Sci.* (*U.S.A.*) 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. Sequence identity may be calculated on the basis of residues identical to a reference sequence. For example, for P16 (SEQ ID NO: 1), having 8 residues, one may have 5 identical residues and have ⅝ or 62.5 (63%) sequence identity. Because of the limited length of the peptides, at least 63% identity is considered "essentially identical" when changes are made according to the present teachings. One may also have ⅝ (75%) or ⅞ (88%) sequence identity. As a further example, a residue may be eliminated, such as R (arginine) may be changed to K, or Y or W may be changed to F and one would have and have ⅞ or 88% identity.

The terms "substantial identity," or "substantial sequence identity," as used herein denotes a characteristic of a polypeptide sequence, wherein the polypeptide comprises a sequence that has at least 60 percent sequence identity, preferably at least 85 percent identity and often 90 to 95 percent sequence identity, or up to 98 or 99 percent sequence identity as compared to a reference sequence over a comparison window of the entire peptide length. Substantial identity further involves a conservative substitution of an amino acid. The term "essentially identical" in the context of the present 6 or 8 residue peptides means that one up to three amino acid substitutions are permitted, e.g. one substitution, according to the present teachings specifically providing guidance in making substitutions, and the definition above.

Conservative amino acid substitutions are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; phenylalanine, tryptophan, and tyrosine are an aromatic family, and cysteine and methionine as a sulfur-containing side chain family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Preferred conservative amino acid substitution groups are: valine-leucine-isoleucine, phenylalanine-tyrosine, lysine-arginine, alanine-valine, glutamic acid-aspartic acid, cysteine-methionine, and asparagine-glutamine.

As further guidance in making amino acid substitutions, one may substitute by changing a given residue to R, or F to increase binding properties, or change it to V, A, L, M or I to increase inhibitory properties. One may direct one part of the peptide to binding to the tyrosinase enzyme, and another part towards inhibition. It is generally preferred not to change F or R and to change K or E, as well as Y or W. Changes to Y should be considered in the context of the overall sequence, since t is the residue that is the natural substrate for tyrosinase. It should be noted that some changes may in fact result in an increase of tyrosinase activity. See, for further guidance, Schurink et al., "Novel peptides with tyrosinase inhibitory activity," *Peptides* 28:485:495 (January 2007).

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The term "topical application," as used herein, means to apply or spread the compositions of the present invention onto the surface of the keratinous tissue.

The term "dermatologically-acceptable," as used herein, means that the compositions or components thereof so described are suitable for use in contact with mammalian keratinous tissue without undue toxicity, incompatibility, instability, allergic response, and the like.

The term "injectable formulation," as used herein, means a formulation suitable for injection into humans and/or animals, wherein the injection is intradermal, subcutaneous, intramuscular or intravenous. These formulations will be sterile, pyrogen free, and at a physiologically acceptable pH.

The term "radiation process," as used herein, means a treatment process as applied to a subject's skin or internal tissue, and is used for cosmetic or therapeutic purposes. The term includes the use of electromagnetic radiation devices, such as lasers, LEDs, radiofrequency, etc. The term also includes the use of ultrasound devices. These devices all are used in processes in which skin whitening using the present agents may be carried out. Some of these processes alter the stratum corneum permeability, and would be beneficially useful in a process of administering the present peptides. Ultrasound may be used to enhance peptide uptake by the skin. Laser treatment may include use of a Q-switched ruby laser (694 nm) or he Q-switched Nd:YAG laser (1064 nm) for the treatment of hyperpigmented lesions such as lentigines and postinflammatory hyperpigmentation.

The term "$IC_{50}$," as is understood in the art, means the means the concentration of tyrosinase inhibitor peptide required to effect 50% inhibition of tyrosinase activity, as conducted in an in vitro assay; a value of "less than" a certain concentration includes $IC_{50}$ values at lower concentrations. The term about may encompass plus or minus 10% variation, and variations resulting from different reagents, experimental conditions, etc. In vitro determinations of $IC_{50}$ using a purified tyrosinase preparation (e.g., mushroom tyrosinase) are useful in determining a clinical dose.

The term "nontoxic" means, in connection with a tyrosinase inhibitor peptide, that it is not toxic to human melanocytes at relatively high concentrations, e.g. concentrations up to 2 mM of peptide in culture over several days.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like. Heterocycles may also be bridged or fused to other cyclic groups.

The term "therapeutically effective amount" is intended to mean the amount of peptide drug sufficient to produce a tyrosinase inhibitory effect applied to a melanocyte, resulting in reduction or elimination of the production of melanin. These amounts are known in the art or may be determined by methods known in the art, and typically range from about 1 to 20,000 mg per human adult and preferably about 10 to 10,000 mg and most preferably range from about 20 to 5,000 mg of the inhibitory agent per application, depending upon the formulation chosen, and whether the tissue, such as the skin or mucous membrane is the site of action.

General Method and Materials

The present materials and methods relate to peptides, which inhibit tyrosinase activity and may be formulated for application to humans. They thus are useful in treatment or amelioration of conditions involving over production of melanin, such as lightening skin pigmentation. Discovery of short sequence peptides with activity against specific enzymes represents an important strategy for the development of future pharmaceutical therapies. Short sequence peptides offer several advantages over traditional pharmacological drugs and growth factors including increased skin penetration, amenability to liposomal encapsulation or lipid conjugation, and reduced toxicity. The present peptides generally will be purified and/or isolated from contaminating biological materials. Purified peptides are then formulated as described below.

Peptides

The present peptides include peptide analogues or peptide derivatives or peptidomimetics that retain the ability to inhibit a tyrosinase activity within a cell. For example, an inhibitory peptide tyrosinase modulator of the invention may be modified to increase its stability, bioavailability, solubility, etc. The terms "peptide analogue," "peptide derivative" and "peptidomimetic" are used herein to include molecules that mimic the chemical structure of a peptide and retain the functional properties of the peptide. Approaches to designing peptide analogs are known in the art. For example, see Farmer, P. S. in Drug Design (E. J. Ariens, ed.) Academic Press, New York, 1980, vol. 10, pp. 119-143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. Examples of peptide analogues, derivatives and peptidomimetics include peptides substituted with one or more benzodiazepine molecules (see e.g., James, G. L. et al. (1993) Science 260:1937-1942), peptides with methylated amide linkages and "retro-inverso" peptides (see U.S. Pat. No. 4,522,752 by Sisto). Peptide analogues, peptide derivatives and peptidomimetic are described in further detail below.

Peptides of the present invention may comprise residues from any of the naturally-amino acids, or from non-naturally-occurring amino acids. These naturally-occurring and non-naturally-occurring amino acids may be in the D or L configuration. The terms D and L are used herein as they are known to be used in the art. Peptides of the invention include single amino acids and short spans (e.g., 1-10) of amino acids. In addition, modified peptides of the present invention may also comprise a monomer or dimer.

The standard single letter and three letter codes for amino acids are used herein and are as follows:

| | | |
|---|---|---|
| A (Ala) Alanine | C (Cys) Cysteine | D (Asp) Aspartic acid |
| E (Glu) Glutamic acid | F (Phe) Phenylalanine | G (Gly) Glycine |
| H (His) Histidine | I (Ile) Isoleucine | K (Lys) Lysine |
| L (Leu) Leucine | M (Met) Methionine | N (Asn) Asparagine |
| P (Pro) Proline | Q (Gln) Glutamine | R (Arg) Arginine |
| S (Ser) Serine | T (Thr) Threonine | V (Val) Valine |
| W (Trp) Tryptophan | Y (Tyr) Tyrosine | |

As described above, the indicated residues may be the naturally occurring L amino acid, or a modification thereof, that is, a chemical modification, an optical isomer, or a link to a modifying group. It is contemplated that specific modifications may be made within the peptide that maintain the ability of the present peptides to specifically inhibit the activity of tyrosinase whereby it catalyzes the first two steps in the pathway for pigment synthesis: hydroxylation of the amino acid tyrosine into dihydroxyphenylalanine (DOPA) and/or the subsequent oxidation into dopaquinone It is also contemplated that specific modifications may be made in a particular sequence in order to confer some additional desirable property to the peptide. Certain amino acids may be substituted for other amino acids in a protein structure without appreciable loss of peptide activity. Since it is the interactive capacity and nature of a peptide that defines that peptide's biological functional activity, certain amino acid sequence substitutions can be made even in a short peptide sequence and nevertheless obtain a peptide with like properties. It is thus contemplated by the inventor that various changes may be made in the sequence of the present tyrosinase inhibitors without appreciable loss of biological utility or activity and perhaps may enhance desired activities.

For example, in designing peptide constructs with tyrosinase inhibitory properties, substitutions may be used which modulate one or more properties of the molecule. Such variants typically contain the exchange of one amino acid for another at one or more sites within the peptide. For example, certain amino acids may be substituted for other amino acids in a peptide structure in order to enhance the interactive binding capacity of the structures. One may also substitute D- for L-amino acids, or include certain side chain covalent modifications.

In making such changes, the hydropathic index of amino acids may be considered.

The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

In modifying the presently exemplified sequences, certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those that are within ±1 are particularly preferred, and those within ±0.5 are even more particularly preferred.

Substitution of like amino acids can also be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In modifying the exemplified sequences, amino acid substitutions may also be generally based on the relative similarity of the amino acid side-chain substituents, for example, their hydrophobicity, hydrophilicity, charge, size, and the like but may nevertheless be made to highlight a particular property of the peptide. Exemplary substitutions that take various of the foregoing characteristics into consideration are well known to those of skill in the art and include: arginine and lysine, which, with histidine, are basic at physiological pH; glutamate and aspartate (which are acidic); serine and threonine; glutamine and asparagine; and valine, leucine and isoleucine.

The naturally occurring amino acid side chains are illustrated below, in which * represents the attachment point to the compound's backbone:

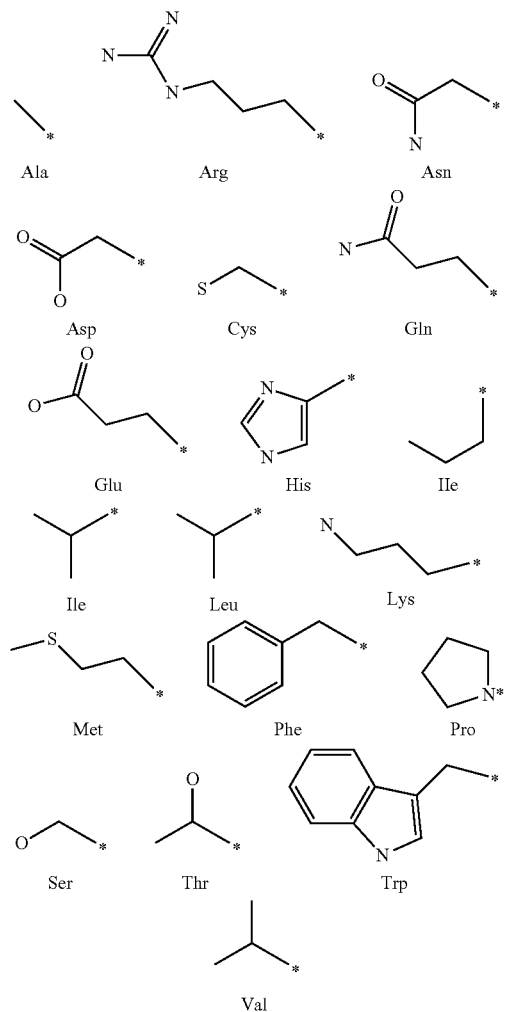

The amino acids of the peptides of the present invention may also be modified so that amino groups may be acylated, alkylated or arylated. Benzyl groups may be halogenated, nitrosylated, alkylated, sulfonated or acylated.

Various chemically modified amino acids may be incorporated into the present peptides. Examples of these include:

Acetylated
N-acetyl-L-alanine, N-acetyl-L-arginine; N-acetyl-L-asparagine; N-acetyl-L-aspartic acid; N-acetyl-L-cysteine; N-acetyl-L-glutamine; N-acetyl-L-glutamic acid; N-acetylglycine; N-acetyl-L-histidine; N-acetyl-L-isoleucine; N-acetyl-L-leucine; N2-acetyl-L-lysine; N6-acetyl-L-lysine; N-acetyl-L-methionine; N-acetyl-L-phenylalanine; N-acetyl-L-proline; N-acetyl-L-serine;
N-acetyl-L-threonine; N-acetyl-L-tryptophan; N-acetyl-L-tyrosine; N-acetyl-L-valine.

Amidated
L-alanine amide, L-arginine amide

Formylated
N-formyl-L-methionine

Hydroxylated
4-hydroxy-L-proline

Lipid Modified
S-farnesyl-L-cysteine, S-geranylgeranyl-L-cysteine, N-palmitoyl-L-cysteine,
S-palmitoyl-L-cysteine, N-myristoyl-glycine, N6-myristoyl-L-lysine Methylated
N-methyl-L-alanine, N,N,N-trimethyl-L-alanine, omega-N, omega-N-dimethyl-L-arginine L-beta-methylthioaspartic acid, N5-methyl-L-glutamine, L-glutamic acid 5-methyl ester 3'-methyl-L-histidine, N6-methyl-L-lysine, N6,N6-dimethyl-L-lysine, N6,N6,N6-trimethyl-L-lysine, N-methyl-L-methionine, N-methyl-L-phenylalanine Phosphorylated
omega-N-phospho-L-arginine, L-aspartic 4-phosphoric anhydride, S-phospho-L-cysteine, 1'-phospho-L-histidine, 3'-phospho-L-histidine, O-phospho-L-serine, O-phospho-L-threonine, O4'-phospho-L-tyrosine Other
L-selenocysteine, L-selenomethionine, L-3-oxoalanine, 2-pyrrolidone-5-carboxylic acid, L-glutamyl 5-glycerylphosphorylethanolamine, 2'-[3-carboxamido-3-(trimethylammonio) propyl]L-histidine (diphthamide), N6-biotinyl-L-lysine,
N6-(4-amino-2-hydroxybutyl)-L-lysine (hypusine), N6-retinal-L-lysine Other modifications to the amino acids contained in the present peptides are known in the art, and described, for example in Kuhner et al. U.S. Pat. No. 6,858,581, which describes chemically modified antimicrobial peptides.

Modulating Groups

In a tyrosinase inhibitor of the invention having the formula shown above, a modulating group for improved cellular uptake or efficacy or formulation may be attached directly or indirectly to the peptide. For example, the modulating group can be directly attached by covalent coupling to the peptide or the modulating group can be attached indirectly by a stable non-covalent association. In one embodiment of the invention, the modulating group is attached to the amino-terminus of the peptide of the modulator. Alternatively, in another embodiment of the invention, the modulating group is attached to the carboxy-terminus of the peptide of the modulator.

In yet another embodiment, the modulating group is attached to the side chain of at least one amino acid residue of the peptide of the compound (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Further guidance on preparing such modulating groups is found in U.S. Pat. No. 5,854,204.

The present peptides may also be conjugated to other tyrosinase inhibitors such as kojic acid (C6H6O4; 5-hydroxy-2-(hydroxymethyl)-4-pyrone) or gnetol (see *Biosci Biotechnol Biochem.* 2003 March; 67(3):663-5.)

Another modulating group for enhancing cell permeability is an amino acid sequence, which is recognized and taken up by melanocytes. D'Ursi et al., "A Membrane-Permeable Peptide Containing the Last 21 Residues of the GS Carboxyl Terminus Inhibits GS-Coupled Receptor Signaling in Intact Cells: Correlations between Peptide Structure and Biological Activity," *Mol Pharmacol* 69:727-736, 2006 disclose cell-penetrating peptides which are able to transport covalently attached cargoes such as peptide or polypeptide fragments of endogenous proteins across cell membranes. The authors coupled their peptide to the 16-residue fragment penetratin, and such fragment may be coupled to the peptides disclosed here.

Thus, the term modulating group means a small organic molecule linked to the peptide to affect its activity, either by improving its stability uptake or the like, or by providing additional tyrosinase inhibition.

In a preferred embodiment, the modifying group(s) comprises a cyclic, heterocyclic or polycyclic group. The term "cyclic group," as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN, or the like.

In another preferred embodiment, the modulating group comprises a fatty acid bonded to the peptide, in order to increase uptake through the skin. Suitable fatty acids (which are meant to include the corresponding ester) include fatty acid ester emollient selected from the group consisting of methyl palmitate, methyl stearate, isopropyl laurate, isopropyl myristate, isopropyl palmitate, ethylhexyl palmitate, lauryl lactate and cetyl lactate.

Formulations

The peptides of the present invention are preferably formulated into topical compositions that contain a dermatologically acceptable carrier. The phrase "dermatologically-acceptable carrier", as used herein, means that the carrier is suitable for topical application to the keratinous tissue, has good aesthetic properties, is compatible with the actives of the present invention and any other components, and will not cause any untoward safety or toxicity concerns. A safe and effective amount of carrier is from about 50% to about 99.99%, preferably from about 80% to about 99.9%, more preferably from about 90% to about 98%, and even more preferably from about 90% to about 95% of the composition.

The carrier can be in a wide variety of forms. For example, emulsion carriers, including, but not limited to, oil-in-water, water-in-oil, water-in-oil-in-water, and oil-in-water-in-silicone emulsions, are useful herein.

Preferred carriers contain an emulsion such as oil-in-water emulsions, water-in-oil emulsions, and water-in-silicone emulsions.

Emulsions according to the present invention generally contain a solution as described above and a lipid or oil. Lipids and oils may be derived from animals, plants, or petroleum and may be natural or synthetic (i.e., man-made). Preferred emulsions also contain a humectant, such as glycerin. Emulsions will preferably further contain from about 0.01% to about 10%, more preferably from about 0.1% to about 5%, of an emulsifier, based on the weight of the carrier. Emulsifiers may be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's Detergents and Emulsifiers, North American Edition, pages 317-324 (1986).

The emulsion may also contain an anti-foaming agent to minimize foaming upon application to the keratinous tissue. Anti-foaming agents include high molecular weight silicones and other materials well known in the art for such use.

Suitable emulsions may have a wide range of viscosities, depending on the desired product form. Exemplary low viscosity emulsions, which are preferred, have a viscosity of about 50 centistokes or less, more preferably about 10 centistokes or less, still more preferably about 5 centistokes or less.

Preferred water-in-silicone and oil-in-water emulsions are described in greater detail in US PGPUB 20060188462 by Bissett et al., published Aug. 24, 2006, entitled "Skin care compositions containing a sugar amine."

The present peptides may be formulated in liposomes. The present peptides may be contained in liposomes according to methods, for example, as described in U.S. Pat. No. 4,944,948 to Uster, et al., entitled "EGF/Liposome gel composition and method," where one substitutes inhibitory peptide for the EGF used there. As described there, a high-viscosity aqueous dispersion of negatively charged liposomes may be prepared with liposome-entrapped peptide. The peptide/liposome composition is formed by suspending a lipid mixture typically containing equimolar amounts of neutral and negatively charged phospholipids and cholesterol in a low-conductivity aqueous medium containing peptide and a zwitterionic compound whose isoelectric point is between pH 5.5 and 8.5 to form a gel-like composition. Further exemplary guidance may be found in U.S. Pat. No. 4,485,054 to Mezei, et al., entitled "Method of encapsulating biologically active materials in multilamellar lipid vesicles (MLV)."

The present peptide tyrosinase inhibitors may also be prepared as an oral or injectable formulation. The pH of the injectable formulation is important, especially in regard to safety and comfort during injection, and especially if the preparation is supplied in a liquid formulation. A suitable formulation may contain preservatives, such as sodium benzoate, methylparaben and propylparaben, etc., and may have a pH of 6.8-8.0 at 25° C. The pH is preferably maintained by a buffer. Suitable buffering agents include acetate buffers, 2-amino-2-methyl-1-propanol, glycine buffers, phosphate buffers, (tris>hydroxymethyl-aminomethane) (TRIS) buffers, (2->N-morpholino-ethanesulfonic acid), etc. The formulation will typically also comprise a carrier as defined above. Injectable formulations are suitable for use in the treatment of melanomas and other cancers that derive from cells expressing tyrosinase, e.g., glioblastomas. Further details may be found in U.S. Pat. No. 5,773,291 to Bouchard, et al., issued Jun. 30, 1998, entitled "Non-melanotytic mammalian cell constitutively expressing biologically active human tyrosinase and use thereof." These formulations are useful with melanocytes not approachable by topical application, such as melanocytes found in non-keratinous tissue. Melanocytes are found in the basal layer of the epidermis as well as in hair follicles, the retina, uveal tract, and leptomeninges. These cells are the sites of origin of melanoma. Regarding oral formulations, an exemplary formulation may be found in US 2007/0134279.

The present peptide tyrosinase inhibitors may be used alone or in combination with each other. They may also be used in combination with other biologically active drugs or cosmeceuticals. They may be delivered by liposomes or other transdermal delivery mechanism, such as disruptive devices etc. A fatty acid chain may be conjugated to the C-terminus or N-terminus of the peptide to promote non-liposomal based delivery via lipid partition into the stratum corneum. Other lethal or suicide agents may be conjugated to the peptides allowing delivery of a lethal or suicide agent to those cells that express tyrosinase at high levels, such as melanoma cells.

Lipid peptide formulations of the present peptides are further described in U.S. Pat. No. 6,287,590 to Dasseux, issued Sep. 11, 2001, entitled "Peptide/lipid complex formation by co-lyophilization;" U.S. Pat. No. 5,543,389 to Yatvin, et al., issued Aug. 6, 1996, entitled "Covalent polar lipid-peptide conjugates for use in salves," and other references.

The length of the oligopeptides described herein, i.e., preferably 8 or less amino acids, with biological inhibitory activity against tyrosinase, has not been previously described. Oligopeptides with activity against tyrosinase have been described in US Patent Publication 20090099091 titled "Oligopeptide Tyrosinase Inhibitors and Uses Thereof", published Apr. 16, 2009 and in US Patent publication 20090099093 titled "Peptide Tyrosinase Inhibitors and Uses Thereof", published Apr. 16, 2009, both of which are also hereby incorporated by reference.

Further guidance on formulating the present peptides may be found in US 20040086560 by Chaudhuri, et al., published May 6, 2004, entitled "Skin-lightening."

The present peptides may further be formulated with other ingredients useful in treating or ameliorating skin conditions, or with ingredients that reduce irritation when the peptides are administered in conjunction with an abrasive procedure. Examples of these additional ingredients, termed here "secondary treatment agents," include 1 percent vitamin K, and 1 percent hydrocortisone in a aqueous base); acne treatment formulations (e.g., salicylic acid, alcohol base buffered by witch hazel, etc.); fine lines/wrinkle treatment formulations (e.g., hyaluronic acid is an aqueous base); hydrating formulations (e.g., calendula, vitamins A, D, or E, or any combination, in a mineral oil base); antioxidant formulations/free radical; scavengers (e.g., vitamins A, E, and K in a mineral oil base). Other examples of product categories that may be employed alone or in combination with other compounds include, antiseptics, astringents, cleansers, pore decongestants, balms, botanicals, collagen stimulators, herbs, microemulsifiers, oxygen delivery vehicles, proteins, serums, skin firming agents, toners, and topical anesthetics. Individually named products as may be used (with associated benefit indicated parenthetically) include: aloe vera (calming); alpha hydroxy acids (peel); alphalipoic acid (antioxidant); benzoil and other peroxides (acne); ceramide (hydrator); copper (toning); copper peptide (toning); CoQ-10 (coenzyme Q-10) and other enzymes (toning); cortisone (calming); glycolic acids (peel); hyaluronic acid (collagen stimulation); hydrolipids (hydrator); lactic acids (peel); magnesium ascorbic phosphate (free radical scavenger, collagen stimulator, bleaching); niacin (vascular dilation); phospholipids (moisturization); potassium (toning, psoriasis), and salicylic acids (acne). The above ingredients are taught for use in conjunction with US PGPUB 20070088371 to Karasiuk, published Apr. 19, 2007, entitled "Microdermabrasion System and Method of Use."

As further secondary treatment agents, the tyrosinase inhibitor peptides and formulation of the present invention can also be optionally mixed with each other and with other skin whitening agents for purposes of treatment, i.e., skin lightening or whitening. For example, the skin whitening products which can be combined include but are not limited to cysteine, 4-thioresorcin, 3-aminotyrosine, 5-hydroxy-2-hydroxymethyl-γ-pyridone, fomesjaponicus and ganoderma extracts, kojic acid, glabridin, licorice extract, glycyrrhizinic acid, catharanthus roseus extract, proteoglycans, proteinase inhibitors, oligopeptides, betaines, and methyl 4-benzyloxy-2-hydroxybenzoate, 4-benzyloxy-2-hydroxybenzoic acid, etc. The present peptides may also be combined, or combined with other tyrosinase inhibitors, such as isoliquiritigenin chalcone (ILC) or 4,4'-dihydroxybiphenyl (44'-BP) (See, Kim et al., "4,4'-Dihydroxybiphenyl as a new potent tyrosinase inhibitor," *Biol Pharm Bull.* 2005 February; 28(2):323-7.)

Dosage

The present peptide formulations may be prepared in dosage forms designed to provide to a subject in need thereof a therapeutically effective amount of peptide. The main upper limit on the amount of peptide in the composition is that the preparation is substantially free of crystals of inhibitory agent and the amount of solvent used is not sufficient to undesirably affect the properties of the finite composition allowing it to adhere to the desired site of application. Thus, the single ingredient inhibitory peptide contains a therapeutically effective amount of peptide within an effective range. The concentration of peptide has been found experimentally to be suitable when extrapolated from the $IC_{50}$. In general, it is suggested that concentrations above two times $IC_{50}$ would be appropriate for prescription use; below about two times $IC_{50}$ would be suitable for over the counter use. However, formulations may contain up to about 100 times $IC_{50}$, to allow for lack of skin uptake or other losses. At twice $IC_{50}$, 95% tyrosinase inhibition should be achieved. The following table is exemplary:

| Peptide | concentration mM | grams in 1 oz cream |
|---|---|---|
| P16 peptide | 0.476 | 0.0191 |
| P17 peptide | 0.796 | 0.0315 |
| P18 peptide | 0.564 | 0.0227 |

1. The above formulations were prepared essentially as follows:

| INGREDIENT NAME | ACCEPTABLE RANGE | PREFERRED RANGE |
|---|---|---|
| 1. WATER | 1.00-90.00% | 30.00-70.00% |
| 1. *ALOE BARBADENSIS* LEAF JUICE | 1.00-90.00% | 5.00-60.00% |
| 2. CAPRYLIC/CAPRIC TRIGLYCERIDE | 1.00-15.00% | 5.00-10.00% |
| 3. PENTYLENE GLYCOL | 0.50-10.00% | 1.00-5.00% |
| 5. DIGLYCERIN | 0.50-20.00% | 1.00-10.00% |
| 6. BIS-ETHOXYDIGLYCOL CYCLOHEXANE 1,4-DICARBOXYLATE | 0.50-3.00% | 1.00-2.00% |
| 7. DIMETHICONE | 0.50-10.00% | 1.00-5.00% |
| 8. ETHYL ASCORBATE | 0.10-10.00% | 1.00-5.00% |
| 9. SODIUM HYALURONATE | 0.50-90.00% | 5.00-20.00% |
| 10. SODIUM PCA | 0.50-20.00% | 1.00-5.00% |
| 11. CETEARYL ALCOHOL | 0.50-5.00% | 1.00-3.00% |
| 12. DICETYL PHOSPHATE | 0.50-5.00% | 0.50-3.00% |
| 13. CETETH-10 PHOSPHATE | 0.50-5.00% | 0.50-3.00% |
| 14. *GLYCYRRHIZA GLABRA* (LICORICE) ROOT EXTRACT | 0.01-5.00% | 0.10-2.00% |
| 15. SQUALANE | 0.50-10.00% | 1.00-5.00% |
| 16. SCLEROTIUM GUM | 0.20-4.00% | 0.50-2.00% |
| 17. DECAPEPTIDE-12 | | |
| 18. BUTYLENE GLYCOL | 1.00-30.00% | 3.00-10.00% |
| 19. PANTHENOL | 0.10-5.00% | 0.50-2.00% |
| 20. ALLANTOIN | 0.01-1.00% | 0.10-0.50% |
| 21. TETRASODIUM EDTA | 0.05-2.00% | 0.10-0.50% |
| 22. CHLORPHENESIN | 0.10-1.00% | 0.10-0.50% |
| 23. CAPRYLYL GLYCOL | 0.10-2.00% | 0.50-1.00% |
| 24. PHENOXYETHANOL | 0.30-2.00% | 0.50-1.00% |

The concentration as well as the quantity of inhibitory peptide per unit area, namely per square or cubic centimeter can be varied independently in order to achieve the desired effect. Higher concentrations of inhibitory peptide base contained in a dosage form of decreased thickness will result in an application of short duration. High concentrations of the inhibitory peptide base contained in a dosage form of increased thickness (higher mg of inhibitory peptide per square or cubic centimeter) will result in potent inhibition with fast onset and long duration. Low concentrations of the inhibitory peptide base in a dosage form of decreased thickness will result in mild inhibition with longer onset and short duration. Low concentrations of the inhibitory peptide contained in a dosage form of increased thickness will have mild inhibition with longer onset and longer duration. As shown in the above explanation, the ability to vary the concentration of inhibitory peptide from very low (about 1%) to high (40% or higher) of the total composition, when combined with the ability to coat thin (about 0.001 inches) or thick (about 0.500 or more inches) enables the practitioner of the invention to vary the dosage of the system as needed for particular anatomical sites of interest.

As a general rule, in the case of a given tissue, e.g., the subepithelial layer, the peptide drug selected, the concentration and thickness and the duration of the application is determined based upon the peptide's ability to penetrate the tissue, for example the basal layer of the epidermis or mucosa, and to be at peak effectiveness within about 2 to 30 minutes. The duration of the effect of the inhibitory peptide on the tissue, for example the epidermis should range between about 2 to 240 minutes, depending on the agent selected, the concentration of the inhibitory peptide and the thickness of application. Longer or shorter durations can also be selected dependent on need, as will be apparent to one skilled in the art.

Methods of Treatment

The present peptides, formulated and/or modified as described above, may be used in a variety of treatment modalities. For example, they may be ingested, injected, or applied in conjunction with laser treatment or dermabrasion/microdermabrasion. Dermabrasion is a cosmetic medical procedure in which the surface of the skin is removed by abrasion (sanding). It is used to remove sun-damaged skin and to remove or lessen scars and dark spots on the skin. Dermabrasion units are typically diamond tipped, although aluminum crystals are also used. One approach, termed "Silk-Peel," combines a diamond tip micro-dermatome with deep delivery of solutions, which may include a whitener to improve and revitalize the skin. In a preferred method, the peptide is administered as part of a solution delivered during microdermabrasion. If the dermabrasion is carried out with a flow of fluids, which surrounds the area of skin being microabraded, the skin is both pretreated and post-treated with the vitamins, lotions, etc., as well as, in a preferred method, the present tyrosinase inhibitor peptide(s). Pretreatment can soften the area of skin treatment to be microabraded, thereby rendering exfoliation more complete and easier to accomplish, with less trauma to the skin tissues left behind, while post-treatment helps to reduce streaking and redness of the skin tissues left behind. Further details on this method of treatment may be found in U.S. Pat. No. 6,695,853 to Karasiuk issued Feb. 24, 2004, entitled "Microdermabrasion system and method of use."

The present peptides may also be used in conjunction with laser treatment. Laser treatments such as the Erbium laser vaporize various depths of damaged skin tissue. Erbium lasers are further described in U.S. Pat. No. 3,978,427. The Erbium laser procedure is performed using topical anesthetic solutions and healing is usually two to five days depending on the depth of laser energy penetration. Based on the absorption spectrum of melanin, the Q-switched ruby laser (694 nm) and the Q-switched Nd: Yag laser (1064 nm) are the lasers of choice for the treatment of hyperpigmented lesions such as lentigines and postinflammatory hyperpigmentation in combination with the present peptides.

The present peptides may be used in conjunction with a variety of radiation treatments in addition to laser treatment, such as administration of radiant energy through Rf devices, LEDs, or ultrasound. The present peptides may also be used microneedle treatment, electroporation or iontophoresis. An appropriate microneedle is described in U.S. Pat. No. 6,256, 533, entitled "Apparatus and method for using an intracutaneous microneedle array," issued on Jul. 3, 2001 to Garstein et al. Electroporation involves the application of high voltage pulses to the skin which has been suggested to induce the formation of transient pores. High voltages and short treatment durations (milliseconds) are most frequently employed. Other electrical parameters that affect delivery include pulse properties such as waveform, rate and number, and are further described in a number of publications. The technology has been successfully used to enhance the skin permeability of molecules with differing lipophilicity and size (i.e., small molecules, proteins, peptides and oligonucleotides). Iontophoresis involves the application of a low level electric current either directly to the skin or indirectly via the dosage form in order to enhance permeation of a topically applied therapeutic agent. Increased drug permeation as a result of this methodology can be attributed to either one or a combination of the following mechanisms: Electro-repulsion (for charged solutes), electro-osmosis (for uncharged solutes) and electro-perturbation (for both charged and uncharged). Several iontophoretic systems are currently under commercial development.

In addition to or included with the above mentioned disorders for which this invention can be of use, are without limitation: freckles reduction, reduction of yellow mass-tone on Asians skins and inhibition of skin, dischromia related to the aging process, as well as a reduction in redness linked to venous disorders and a reduction in UV-induced pigmentation.

As described above, a preferred method of treatment involves the lightening of skin. The present inhibitors may also be used for other treatments. Tyrosinase is an attractive target antigen for immunotherapeutic treatment of patients with melanoma because it is more homogeneously expressed than several other melanocyte differentiation antigens such as MART-1, gp100, or gp75. In two separate investigations, tyrosinase was found to be expressed in 100% of fresh melanoma specimens evaluated by immunohistochemistry or reverse transcription-polymerase chain reaction. These data indicate that tyrosinase may be an excellent target for essentially all patients with melanoma (Riley et al., *J. Immunother.*, 2001, 24, 212-220).

Tyrosinase has also been implicated in Vogt-Koyanagi-Harada (VKH) disease. VKH is a bilateral granulomatous panuveitis associated with central nervous system, auditory, and integumentary manifestations. It usually manifests with prodromal similar to asceptic meningitis, followed by posterior uveitis with exudative retinal detachments and disk hyperemia. T-cell clones established from patients with VKH disease and stimulated with tyrosinase family peptides demonstrated a predominantly proinflammatory, Th1-type T-cell response. Read et al. demonstrated that a VKH-like syndrome is inducible in rats by immunization with peptides derived from tyrosinase and other tyrosinase family proteins (Read et al., *Curr. Opin. Ophthalmol.*, 2000, 11, 437-442).

EXAMPLES

Modeling of Enzyme-Substrate Complexes by Automated Molecular Docking

Molecular docking of the peptides and HQ into the 3-D X-ray structure of the Met1 form of *S. castaneoglobisporus* tyrosinase (PDB ID: 2ZMX, chain A) (Matoba, Y., Kumagai, T., Yamamoto, A., Yoshitsu, H., and Sugiyama, M. (2006) *J Biol Chem* 281, 8981-8990) was carried out using AutoDock version 4.2.2.1 (Morris, G. M., Huey, R., Lindstrom, W., Sanner, M. F., Belew, R. K., Goodsell, D. S., and Olson, A. J. (2009) *J Comput Chem* 30, 2785-2791) and the newer AutoDock Vina version 1.0.3 (Trott, O., and Olson, A. J. *J Comput Chem* 31, 455-461). Molecular docking images were visualized using PyMOL version 0.99rc6 (Schallreuter, K. U. (2007) *Dermatol Clin* 25, 283-291, vii; DeLano, W. L. (2002) *Curr Opin Struct Biol* 12, 14-20). The rigid molecule of tyrosinase was prepared using Swiss-PdbViewer version 4.0 (Guex, N., and Peitsch, M. C. (1997) *Electrophoresis* 18, 2714-2723) and AutoDockTools version 1.5.4 to fix missing hydrogens, remove $NO_3$ molecules, water molecules, and assign Gastiger charges. The copper ions were added to the parameter file and reintroduced in the pdbqt file prior to running AutoGrid and AutoDock. The HQ molecule was obtained from the PubChem Compound Database (Wang, Y., Xiao, J., Suzek, T. O., Zhang, J., Wang, J., and Bryant, S. H. (2009) *Nucleic Acids Res* 37, W623-633). The oligopeptides were created using the Avogadro version 1.0.0 and exported as pdb files. The ligand files were prepared using the PRODRG2 server (Schuttelkopf, A. W., and van Aalten, D. M. (2004) *Acta Crystallogr D Biol Crystallogr* 60, 1355-1363) and AutoDockTools to assign charges and torsions. All possible torsions were allowed for each ligand.

Docking Simulation of Octapeptides and HQ

A new series of shorter chain length oligopeptides (≤8 amino acids) was designed, all of which included multiple arginines to enhance cell penetration (see below). The oligopeptides were devoid of sulfhydryl residues, except P15, which included 2 cysteines to determine the impact of these residues on potency. The choice of amino acids was further influenced by previous studies such as Ishikawa et al (Biol. Pharm. Bull., 2007, 30: 677-681) who reported that a combination of amino acids alanine, glycine, isoleucine and leucine were important for tyrosinase inhibition. Schurink et al (Peptides, 2007, 28: 485-495) who found that tyrosinase inhibition is optimal when arginine and/or phenylalanine is/are combined with hydrophobic aliphatic residues such as valine, alanine or leucine. In addition they proposed that peptides should contain one or more arginine residues for strong tyrosinase inhibitory and binding activity.

Oligopeptides were initially screened using a molecular docking simulation program to assess their affinity for the tyrosinase catalytic site. Since HQ's binding free energy was found to be −4.7 kcal/mol, only those oligopeptides with free energy scores less than this value were considered. A total of 6 oligopeptides that met this criterion were found, of which 3 were octapeptides (P16-18) and three were shorter than 8 amino acids in length (P13-15). Results are given in the Table 1 below:

| Peptide | SEQ ID NO: | Amino acid sequence |
|---------|------------|---------------------|
| P13 | 4 | RRVAL |
| P14 | 5 | RRFVLL |
| P15 | 6 | RRFVCC |
| P16 | 1 | RRWWRRYY |
| P17 | 2 | RRRYWYYR |
| P18 | 3 | RRYWYWRR |

All 3 octapeptides were found to have better binding energies than HQ (Table 2, below). Table 2 presents a summary of Autodock simulations of binding energies for HQ and P13-18. Residue in Catalytic Pocket refers to the catalytic site residue that is closest to the copper ions. The number following each amino acid describes its position within the sequence.

TABLE 2

| Compound | SEQ ID NO: | Sequence | Vina binding energy (kcal/mol) | Residue in Catalytic Pocket |
|---|---|---|---|---|
| HQ | — | — | −4.7 | — |
| P13 | 4 | RRVAL | −5.4 | R2 |
| P14 | 5 | RRFVLL | −5.2 | F3 |
| P15 | 6 | RRFVCC | −5.2 | R2 |
| P16 | 1 | RRWWRRYY | −5.8 | W3 |
| P17 | 2 | RRRYWYYR | −6.0 | W5 |
| P18 | 3 | RRYWYWRR | −5.8 | W4 |

P17 showed the best binding energy at −6.0 kcal/mol compared to −5.8 kcal/mol for P16 and P18, and −4.7 kcal/mol for HQ. P13-15 binding energies ranged from −5.2 to −5.4 kcal/mol. Autodock simulations were ran for P16-18 and HQ with tryptophan and tyrosine in the catalytic pocket vicinal to the copper ions (data not shown). Table 3 presents a summary of AutoDock simulations of binding energies for P16-18 fragments. Residue in the Catalytic Pocket refers to the catalytic site residue that is closest to the copper ions. The number following each amino acid describes its position within the sequence.

TABLE 3

| Peptide fragment | Sequence | SEQ ID NO: | Vina Binding Engergy (kcal/mol) | Residue in Catalytic Pocket |
|---|---|---|---|---|
| P16a | RRWWRR | 7 | −5.1 | W4 |
| P16b | RWWR | 8 | −5.6 | W2 |
| P16c | RWWRRY | 9 | −5.5 | W2 |
| P17a | RRYWYY | 10 | −5.4 | Y3 |
| P17b | RYWYYR | 11 | −6.1 | W2 |
| P18a | RRYWYW | 12 | −6.2 | W4 |
| P18b | RYWYWR | 13 | −6.8 | Y4 |
| P18c | YWYWRR | 14 | −5.5 | W4 |

Based on the AutoDock simulations (Tables 2 and 3), tryptophan residues of the octapeptides were observed to be bound inside the catalytic core near the copper ions of tyrosinase. This is consistent with the findings of Noh et al (Bioorg. Med. Chem. Lett., 2009, 19: 5586-5589) who showed the importance of hydrophobic interactions between aromatic amino acids and the hydrophobic side chains at the active site. In addition, similar interactions were noted with most of the remaining aromatic amino acids, as well as arginine residues, confirming an affinity for hydrophobic areas around the catalytic site.

The binding energies for P13-15 were better than for HQ, confirming the importance of the hydrophobic aliphatic residues such as valine, alanine and leucine. Despite their favorable binding energies, P13-15 were weak inhibitors of mushroom tyrosinase. This suggests that binding and inhibitory potency are controlled by different mechanisms. It was found that elimination of 2 C-terminal tyrosine residues weakened binding affinity (Table 3). Further simulations of a tetramer fragment P16b, which lacked the flanking arginine residues, suggested that the presence of 2 consecutive arginines likely results in steric hindrance.

Unlike P13-15, P16-18 showed both favorable binding energies as well as potent tyrosinase inhibitory activity. All 3 octapeptides shared in common the presence of a tryptophan residue, which based on AutoDock simulation appears to reside in the catalytic pocket in great proximity to the copper ions (Table 2). Furthermore, fragments P17a and P18b, which both contained a tyrosine residue, also bound inside the catalytic pocket. On the other hand, P13-15 lacked both tryptophan and tyrosine residues. Altogether, the data suggest that the indole moiety of tryptophan is playing a major role in the inhibitory potency of the octapeptides via copper chelation.

Enzymatic Assay of Mushroom and Human Tyrosinase

Mushroom tyrosinase, L-tyrosine, HQ, and L-dopa were purchased from Sigma Aldrich (St. Louis, Mo.). The peptides (table 1) were synthesized by Bio Basic, Inc (Ontario, Canada) using solid-phase FMOC chemistry. Peptides were confirmed to be of research grade (>80% purity) in all cases. It is understood that research grade reagents were used for convenience, and it is preferred that the peptides be prepared to pharmaceutical grade purity, greater than 90%, preferably greater than 99% pure. The present peptides may be synthesized using a variety of chemistries, preferably solid phase peptide synthesis as described e.g. in Benoiton, "Chemistry of peptide synthesis," CRC Press 2006. Tyrosinase inhibitory activity was determined in vitro using L-tyrosine or L-dopa as the substrate following a modified method from Piao, L. Z., Park, H. R., Park, Y. K., Lee, S. K., Park, J. H., and Park, M. K. (2002) *Chem Pharm Bull* (Tokyo) 50, 309-311. The concentration of enzyme, substrate and inhibitor was denoted as [E], [S] and [I], respectively. The experiment was conducted in a 96-well flat-bottomed plate. Each well contained 80 μl of 0.067 M potassium phosphate buffer (pH 6.8), 40 μl of 5 mg/ml L-tyrosine dissolved in 0.067 M potassium phosphate buffer (pH 6.8), 40 μl of the different concentrations of inhibitors dissolved in the same buffer, and 40 μl of 480 units/ml mushroom tyrosinase solution. The final volume of each well was 200 μl, containing 1 mg/ml [S], 96 units/ml [E] and varying concentrations of [I] ranging from 1 μM to 10 mM. For the negative control wells, the inhibitors were substituted with buffer solution and adjusted to the total volume of 200 μl. HQ served as a positive control to calibrate the assay as a wide range of $IC_{50}$ values has been previously reported (Neeley, E., Fritch, G., Fuller, A., Wolfe, J., Wright, J., and Flurkey, W. (2009) *Int J Mol Sci* 10, 3811-3823). The assay mixture was incubated at 37° C. The optical density of the reaction mixtures, which correlates with the amount of dopachrome produced, was measured at 475 nm using a Varioskan microplate reader (Thermo Electron Corporation, San Jose, Calif.) at different time periods. For assessment of the $2^{nd}$ step of melanin synthesis, we used L-dopa as the substrate and freshly extracted human tyrosinase as previously described (Abu Ubeid, A., Zhao, L., Wang, Y., and Hantash, B. M. (2009) *J Invest Dermatol* 129, 2242-2249).

Kinetic Studies

Experiments were conducted using the same protocol as above except for changes in concentration of [E], [S] and [I]. [E] was 24 units/ml, [S] was 0.05, 0.1, 0.25, 0.5, 0.75 and 1 mM, and [I] was 0, 0.03, 0.1, 0.3 and 1 mM. Lineweaver-Burk reciprocal plots were generated to determine the mode of inhibition (Burk, D., Lineweaver, H., and Horner, C. K.

(1934) *J Bacteriol* 27, 325-340), and Michaelis Menten plots were used to determine $V_{max}$ and $K_m$. Nonlinear regression using GraphPad Prism 5 software was used to determine $K_i$. Prism calculates the $K_i$ using the equation of Cheng, Y., and Prusoff, W. H. (1973) *Biochem Pharmacol* 22, 3099-3108.

Inhibition of Mushroom Tyrosinase by Oligopeptides

Figure 1B:
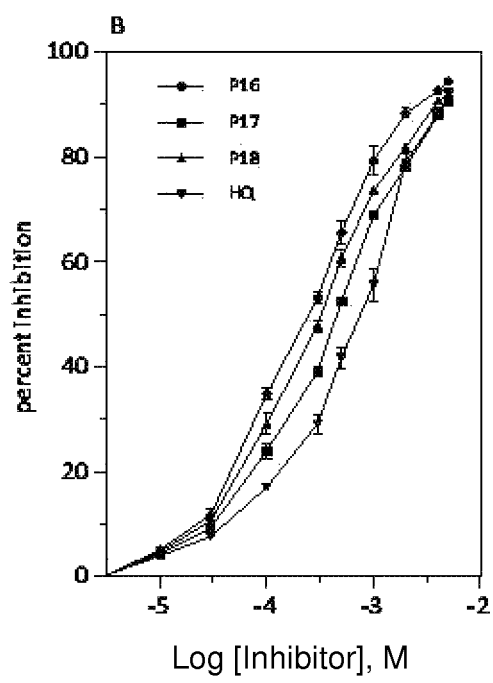
Figure 4:
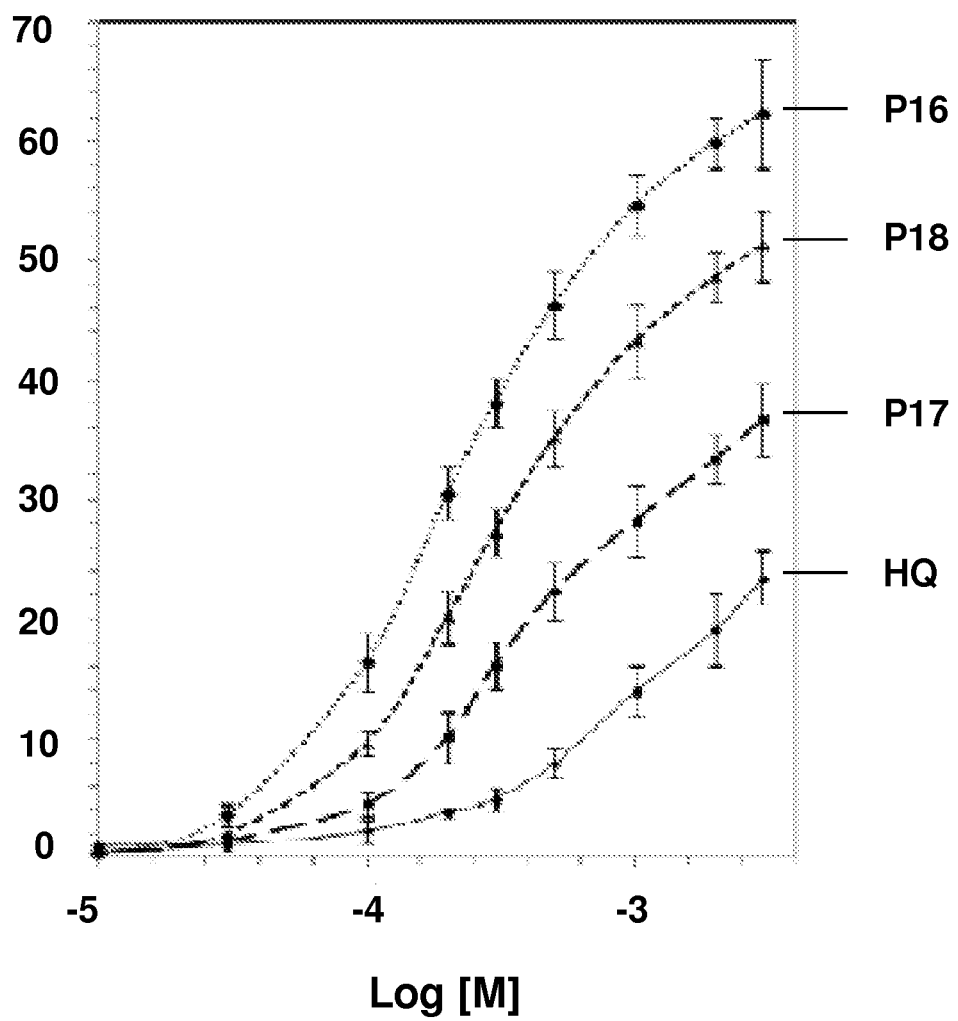
FIG. 4 is a graph of dose-dependent inhibitory effects of octapeptides P16-18 and HQ on freshly extracted human tyrosinase. The effect on human tyrosinase activity by the compounds as a function of concentration is presented as percent inhibition and plotted as means±S.E of 5 independent trials.

Although the free energy values provide insight regarding catalytic site binding affinity, it does not convey on its own information about the inhibitory potential of an oligopeptide. In order to assess this potential, their inhibitory activity against mushroom tyrosinase was tested. Dose response curves for P13-18 and HQ are shown in FIG. 1. The $IC_{50}$ for P16, P17, and P18 was 238, 398, and 282 µM, respectively, compared to 560 µM for HQ (Table 3, above). P13-15 demonstrated weak inhibition of mushroom tyrosinase with $IC_{50}$ values of 2.2, 1.8, and 1.1 mM, respectively (FIG. 1A and Table 4).

tively (Table 4, above). These data suggest that HQ and the octapeptides are competitive inhibitors of tyrosine, Inhibition of Human Tyrosinase by Octapeptides The inhibitory activity of P16-18 (SEQ ID NO: 1, 2 and 3 respectively) and HQ against human tyrosinase was also examined using L-dopa as the substrate. FIG. 4 shows dose-dependent inhibition for all 4 compounds using L-dopa as the substrate. The octapeptides were significantly more potent inhibitors of human tyrosinase relative to HQ. At 200 µM, human tyrosinase activity was reduced by 30% for P16, 12% for P17 and 25% for P18 compared to only 5% for HQ. Similar results were observed when using L-tyrosine as the substrate and L-dopa as the co-factor (data not shown).

The inhibitory activity of P16-18 (SEQ ID NO: 1, 2 and 3 respectively) on human tyrosinase was examined in two settings: 1) using L-dopa as the substrate, and 2) using tyrosine as the substrate with L-dopa as a co-factor. In the latter,

TABLE 4

Summary of the mushroom tyrosinase inhibitory profile for P13-18 and HQ molecular docking simulations of binding energies for P13-18 and HQ. Catalytic pocket residue refers to the residue that is closest to the active site copper (Cu) ions. The number following each amino acid describes its position within the sequence.

| Compound | Sequence | $IC_{50}$ [µM] | $K_i^a$ [µM] | Nature of inhibition[b] | Vina Binding Energy (kj/mol) | Residue in Catalytic Pocket | Cu Ion Distance (Å) |
|---|---|---|---|---|---|---|---|
| HQ | — | 560 ± 12 | n/a | competitive | -19.74 | — | 4.45 and 5.26 |
| P13 | RRVAL | 2200 ± 100 | n/a | n/a | -22.68 | R2 | 4.65 and 4.98 |
| P14 | RRFVLL | 1770 ± 80 | n/a | n/a | -21.84 | F3 | 5.09 and 5.15 |
| P15 | RRFVCC | 1120 ± 50 | 167 ± 11 | n/a | -21.84 | R2 | 4.56 and 5.71 |
| P16 | RRWWRRYY | 238 ± 10 | 190 ± 10 | Competitive | -24.36 | W3 | 4.00 and 4.66 |
| P17 | RRRYWYYR | 398 ± 11 | 179 ± 10 | Competitive | -25.2 | W5 | 4.56 and 5.45 |
| P18 | RRYWYWRR | 282 ± 12 | 205 ± 10 | Competitive | -24.36 | W4 | 4.39 and 5.48 |

[a] Mode of inhibition was derived from the Lineweaver Burk plots.
[b] n/a: not available for P13-P15. One way ANOVA showed that P16-18 $K_i$ values were significantly different from HQ ($p < 0.005$).

Figure 2A:
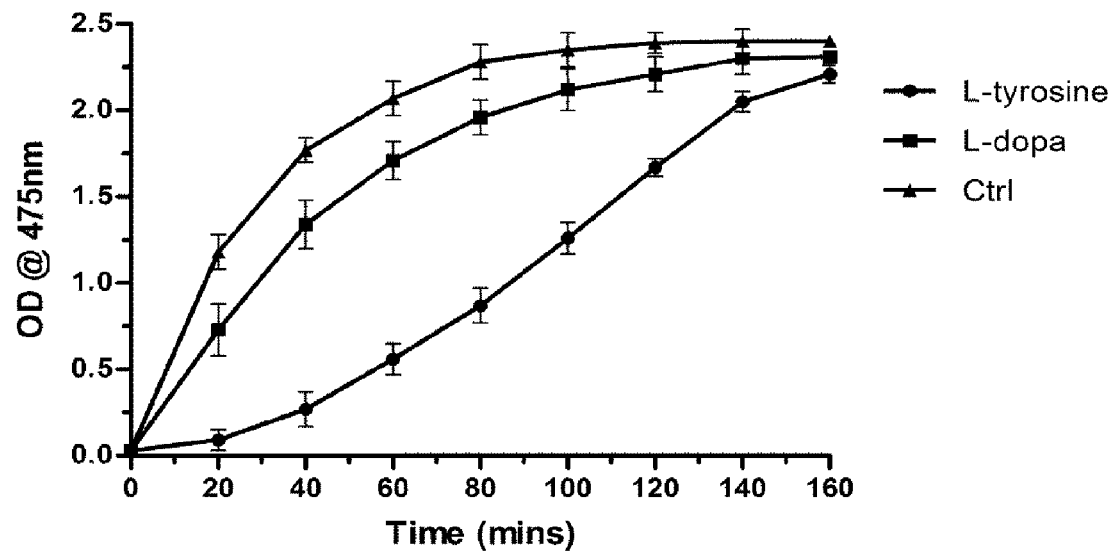
FIGS. 2A and 2B is a pair of graphs showing time response curves for (A) 500 µM HQ with L-tyrosine or L-dopa as substrates in the mushroom tyrosinase assay. The control line is L-dopa without HQ. (B) P16-18 at 300 µM with L-dopa as substrate compared to HQ at 500 µM. Data represents the means±S.E of 5 independent tests.
Figure 2B:
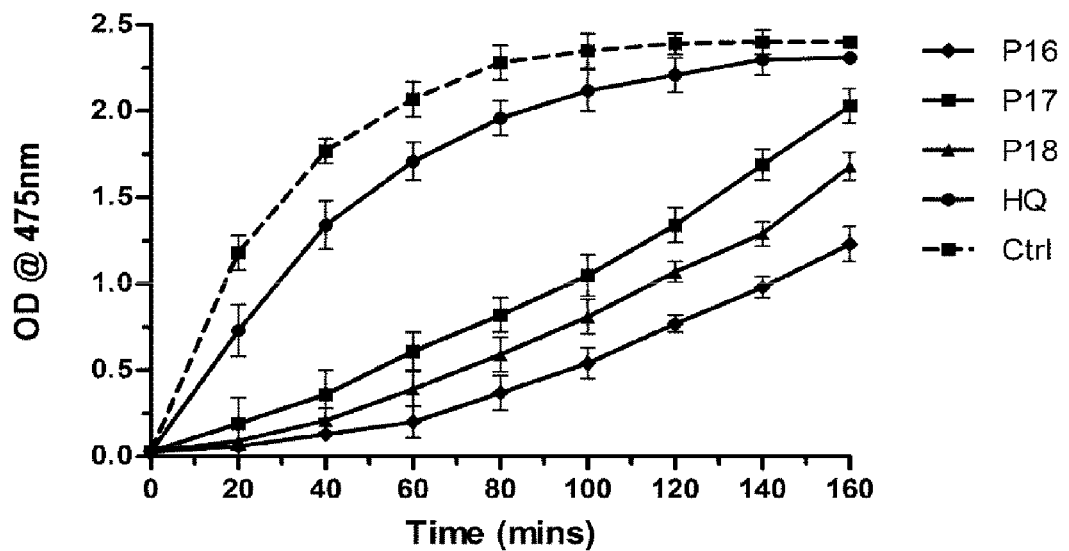

FIG. 1 also illustrates that the inhibitory activity of the oligopeptides was dose-dependent. The inhibitory activity of P16-18 and HQ on the $2^{nd}$ step of melanin synthesis pathway was also tested by replacing L-tyrosine with L-dopa as the substrate. The $2^{nd}$ step of the melanin pathway involves tyrosinase catalysis of L-dopa rather than L-tyrosine. HQ weakly inhibited L-dopa oxidation whereas all 3 octapeptides showed potent inhibition (FIG. 2). Based on these results, further studies were focused on P16-18, Competitive Inhibition of Mushroom Tyrosinase by Octapeptides The kinetics and mode of inhibition for P16-18 (SEQ ID NO: 1, 2 and 3 respectively) and HQ was determined using a standard assay (Pomerantz, S. H. (1966) *J Biol Chem* 241, 161-168). As illustrated by Lineweaver-Burk plots shown in FIG. 3, the $V_{max}$ was independent of substrate concentration for P16-18 and all 3 octapeptides, whereas the $K_m$ was altered. The inhibition constants ($K_i$) for HQ, and P16-18 were determined to be 205 µM, 167 µM, 190 µM and 179 µM respec- L-dopa acts as a hydrogen donor helping eliminate the lag period observed during tyrosine hydroxylation (Pomerantz, S. H., and Warner, M. C. (1967) *J Biol Chem* 242, 5308-5314). This lag period can be eliminated or shortened by adding L-dopa as cofactor, and is explained by the redox state of the extracted enzyme. Depending on the valence of the copper ions in the enzyme's active site, it can exist in 3 intermediate states: deoxy, oxy and a met-form. These 3 states influence the ability of tyrosinase to bind to its substrates and therefore determine the reaction kinetics. The met form of the enzyme is predominant in vivo and is the resting form of tyrosinase. The enzyme as obtained after purification is found to be a mixture of >85% met and <15% oxy forms (Sanchez-Ferrer, A., Rodriguez-Lopez, J. N., Garcia-Canovas, F., and Garcia-Carmona, F. (1995) *Biochim Biophys Acta* 1247, 1-11). In the met-form, the enzyme can catalyze the dehydrogenation of diphenols such as L-dopa to dopaquinone, and in the process, the other forms of the enzyme are replenished. FIG. 4 shows dose-dependent inhibition for all 4 compounds.

We found similar results for both experimental settings (data for L-tyrosine as substrate not shown). It can be seen that all 3 octapeptides were significantly more potent than HQ in their effect on human tyrosinase. At 200 µM, human tyrosinase activity was reduced by 30% for P16, 12% for P17, and 25% for P18 compared to 5% for HQ.

A different activity level of HQ was found when L-dopa was substituted for L-tyrosine as the substrate. This substitution mirrors the substrate encountered by tyrosinase in the $2^{nd}$ step of the melanin pathway. For an inhibitor to be clinically relevant, it must have activity against both steps. When L-dopa was used as the substrate, HQ inhibition was very weak (FIG. 2). These findings support the notion of two binding sites on the enzyme, a hypothesis first put forward by Hearing et al. (Hearing, V. J., and Ekel, T. M. (1976) *Biochem J* 157, 549-557), who argued that there exists one site for tyrosine hydroxylase and another site specific for dopa oxidase activity. The present findings with HQ further support their hypothesis of separate catalytic sites for L-dopa and L-tyrosine (Schallreuter, K. U., Kothari, S., Chavan, B., and Spencer, J. D. (2008) *Exp Dermatol* 17, 395-404; Abu Ubeid, A., Zhao, L., Wang, Y., and Hantash, B. M. (2009) *J Invest Dermatol* 129, 2242-2249). In sharp contrast, no substrate-specific differences in inhibitory activity for the octapeptides were observed.

Melanin Content Measurement

MNTI cells were cultured in 24-well plates and treated with individual test samples for 3 days. Octapeptides P16-18 were tested at double the derived [IC50] and HQ was tested at 50 µM. After 3 days, the media was discarded and the wells were washed with PBS. Cells were detached by short incubation in trypsin/EDTA (0.25%/0.1% in PBS). An aliquot was used for cell counting and the remaining cells were sonicated and incubated overnight in the dark in 500 µL 1M NaOH at 37° C. Melanin concentrations were calculated by comparing the OD at 475 nm of test samples with a standard curve obtained using synthetic melanin (Sigma Aldrich, St Louis, Mo.). The MNTI cell line was derived from a human melanotic neuroectodermal tumor of infancy and was a kind gift from Dr. Vincent Hearing (National Cancer Institute, Bethesda, Md.). MNTI cells were grown in DMEM supplemented with 20% FBS, 10% AIM-V medium, 20 mM Hepes and 1% antibiotic-antimycotic solution (Invitrogen). MNTI total melanin content was measured according to the method discussed previously (A. Abu Ubeid, L. Zhao, Y. Wang, B. M. Hantash, Short-sequence oligopeptides with inhibitory activity against mushroom and human tyrosinase, J Invest Dermatol, 129 (2009) 2242-2249).

Trans-Membrane Penetration of Octapeptides Leads to Reduced Melanin Content

Figure 5:
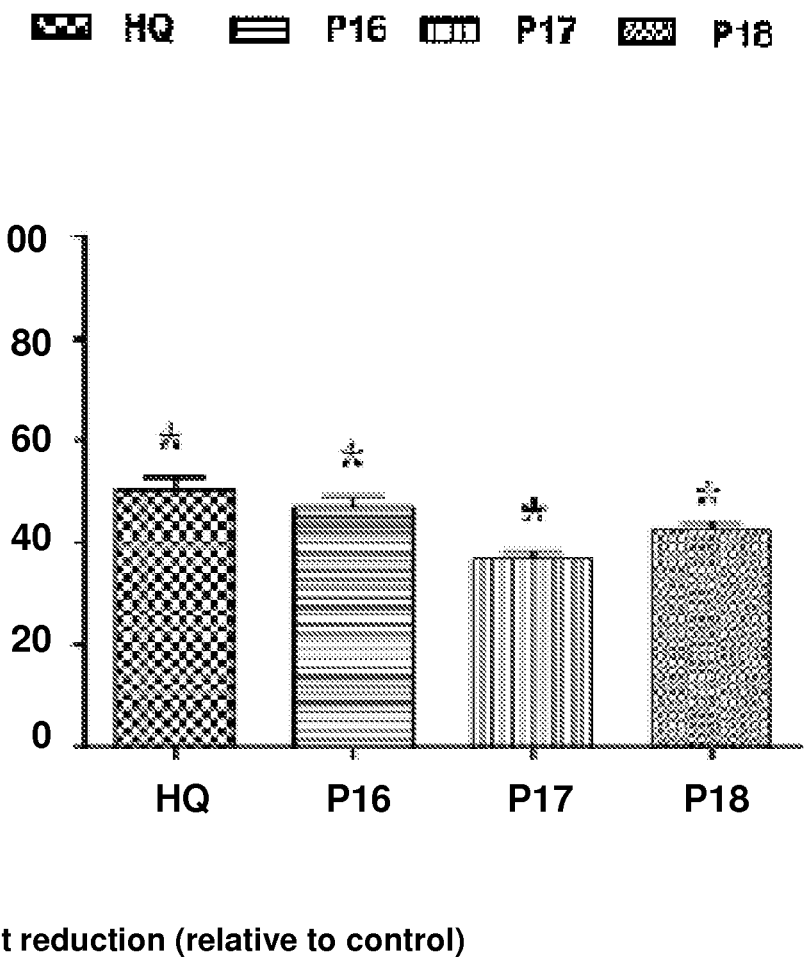
FIG. 5 is a graph showing the effect of HQ and octapeptides P16-18 on melanin content in MNTI cells. After treatment with either 50 µM HQ or octapeptide (at twice the [IC50]) for 3 days, cells were lysed and incubated overnight in 1M NaOH. Melanin content was measures at an OD of 475 nm. Data is shown as % control. *p<0.001.

Although the above results suggested the octapeptides are capable of inhibiting human tyrosinase, it remained unclear if these peptides can successfully penetrate the plasma membrane and load sufficiently into melanosomes to exert their inhibitory effect on tyrosinase. To assess this possibility, pigment-producing human MNTI cells were incubated with octapeptide, HQ, or vehicle for 3 days, and melanin content measured spectrophotometrically. As illustrated in FIG. 5, total melanin content was reduced by 45±2% for P16, 38±2% for P17, and 41±3% for P18. For 50 µM HQ, melanin content was reduced by 50±4%. The octapeptides successfully blocked pigment production in living human melanin-producing cells. This result was significant for 3 reasons: 1) it confirmed that the octapeptides could match HQ's hypopigmenting activity, 2) it showed that the octapeptides possess adequate cell penetration and appropriately translocate to melanosomes, and 3) that unlike HQ, the octapeptides were not limited by dose-dependent cytotoxicity at the concentrations tested in this study.

Statistical Analysis

Each experiment was performed in triplicate and run a minimum of 5 independent times. The results were averaged and standard errors of the mean were calculated for all conditions. One way analysis of variance (ANOVA), student's t test, and computation of kinetics parameters were executed with GraphPad Prism 5.0 software.

Culture of Primary Human Melanocytes, Keratinocytes, and Fibroblasts

Human melanocytes, a generous gift from Dr. Todd Ridky (Stanford University, Stanford, Calif.), were cultured in 100 mm dishes using medium 254 (Invitrogen, Carlsbad, Calif.) incubated at 37° C. in a humidified 5% $CO_2$ chamber. At 80 to 90% confluence, cells were harvested and lysed using 1% Triton X-100 in 0.067 M potassium phosphate buffer (pH 6.8). Cells were then sonicated twice at 20% intensity for 30 s on ice. Lysates were clarified by centrifugation at 10,000 g for 10 min. Protein content was determined using a colorimetric DC protein assay kit (Bio-Rad, Richmond, Calif.). Lysates were added to a 96 well flat-bottomed plate containing equal amounts of protein (40 µg), and adjusted with lysis buffer to reach 150 µL in each well. L-DOPA was dissolved in lysis buffer and added to each well at a final concentration of 2.5 mM. Each triplicate of wells received different concentrations (0 to 3 mM) of oligopeptide or HQ. The plate was incubated at 37° C. for 120 min, and then optical density readings were measured at 475 nm using a Varioskan microplate reader (Thermo Electron Corporation) at 10 min intervals. Certain wells served as controls and contained protein extract without inhibitors or vice versa. Human dermal fibroblasts were purchased from ATCC and cultured in DMEM (Invitrogen) supplemented with 10% fetal bovine serum (FBS, Invitrogen). Human keratinocytes (Invitrogen) were cultured in Epilife medium (Invitrogen).

Viability/Proliferation and Cytotoxicity Assays

Keratinocytes, fibroblast, and melanocyte proliferation rates were determined using a TACS® MTT Cell Proliferation Kit (R&D systems, Minneapolis, Minn.). Cells were plated at 2.5×104/well in 96-well plates in a humidified atmosphere with 5% CO2 at 37° C. Twenty-four h after plating, test samples were added and cultures were incubated for an additional 72 h. The remainder of the procedure was performed following the manufacturer's protocol.

Cellular toxicity was measured using a trypan blue dye exclusion assay. Cells were cultured in 6-well plates at a density of $4 \times 10^5$ cells/well for 1, 3, or 6 d in 2 ml of medium. Each well received a different concentration of peptide or HQ (0, 30, 100, 300, 1000 and 3000 µM), and media and inhibitors were changed every 48 h. The plates were incubated at 37° C. in a humidified 5% CO2 chamber, harvested at the appropriate time, treated with trypan blue, and then counted using a hemacytometer. Cytotoxicity was measured according to the following formula: [1−(# of cells in control−# of live cells in test sample)/# of cells in control]×100%.

Figure 6A:
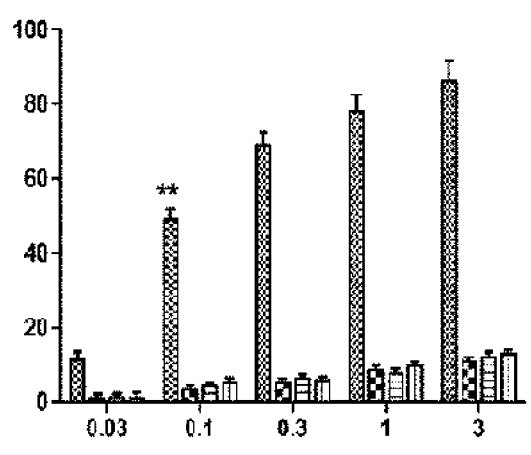
FIGS. 6 A (melanocytes), 6 B (keratinocytes), and 6 C (fibroblasts) are plots of an MTT assay comparing effects of P16-P18 (SEQ ID NOs: 1, 2, and 3 respectively) and HQ on the viability and proliferation of human melanocytes, keratinocytes, and fibroblasts. The three cell types were incubated with varying concentrations of the test compounds for 72 h at 37° C. and then processed using the MTT assay. Data are presented as % toxicity relative to the control as a function of concentration, and plotted as means±S.E of 5 independent trials. **p<0.01.
Figure 6B:
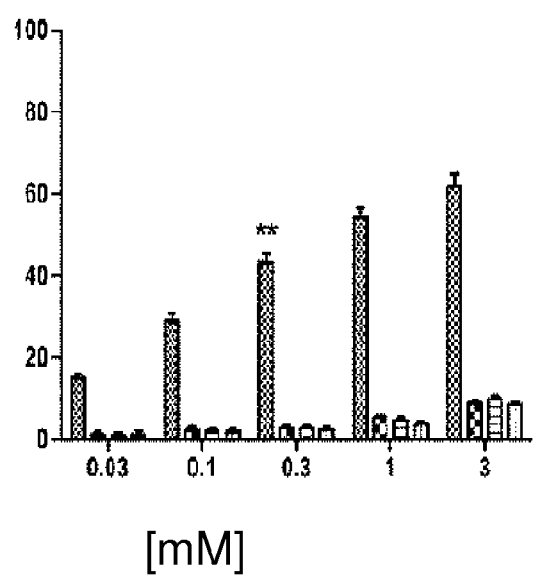
Figure 6C:
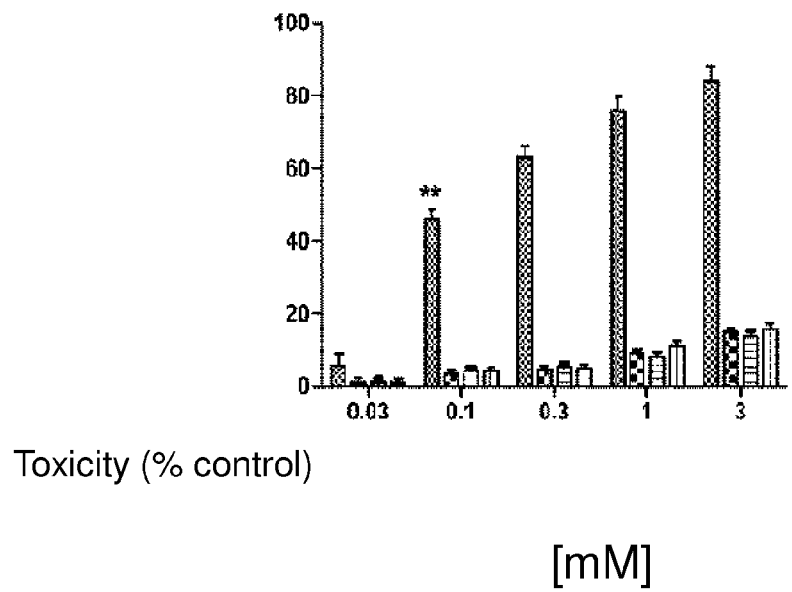

Octapeptides are Minimally Cytotoxic to Human Melanocytes, Keratinocytes, and Fibroblasts To evaluate the effect of P16-18 on viability and proliferation, primary human melanocytes, keratinocytes, and fibroblasts were incubated in the presence or absence of various concentrations of octapeptides or HQ. Proliferation rates were then assessed at 3 d using an MTT assay. FIG. 6 shows that treatment with 100 µM HQ resulted in 30±3%, 45±2%, and 50±3% reduction in keratinocytes, fibroblast, and melanocyte proliferation rates, respectively. Unlike HQ, up to 1 mM of P16-18 resulted in minimal reduction (0-10%) of proliferation relative to untreated controls for the 3 cell types tested. At 3 mM HQ, proliferation was inhibited by over 90% for both melanocytes and fibroblasts, and up to 63±3% for keratinocytes. For 3 mM P16-18, proliferation rates were reduced by 10-12% for all 3 cell types.

Figure 7A:
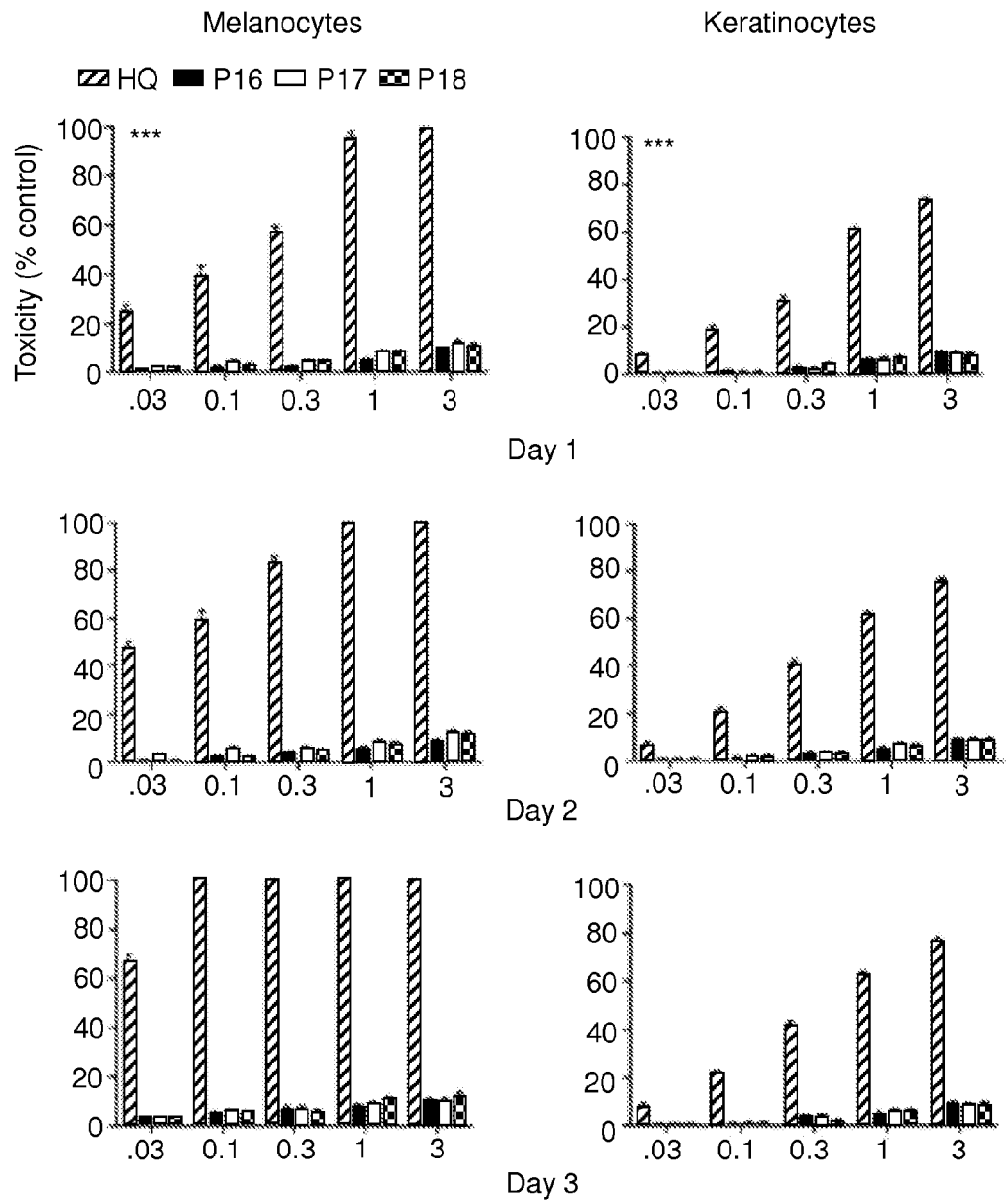
FIGS. 7A and 7B show a set of graphs comparing effects of HQ and P16-18 on human melanocyte, keratinocyte (FIG. 7A), and fibroblast (FIG. 7B) viability on Days 1, 2 and 3 for each of the three cell types. Cells were seeded at equal numbers and incubated with varying concentrations of test samples for 1 day, 3 days and 6 days, harvested, stained with trypan blue, and then counted. The assay was carried out in triplicate, and the % cell death was calculated according to the formula shown in Examples. Data is plotted as means±S.E. of 5 independent trials. ***p<0.001. HQ was significantly more toxic to melanocytes and fibroblasts.
Figure 7B:
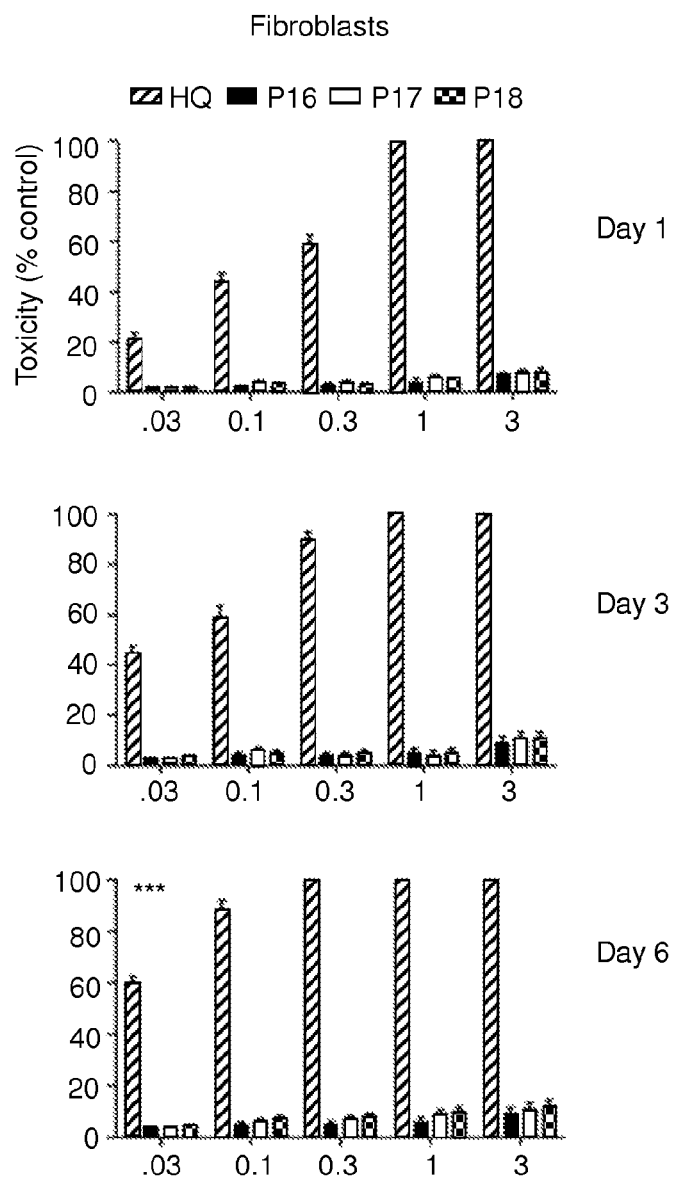

The cytotoxic effect of P16-18 on primary human melanocytes, keratinocytes, and fibroblasts were then assessed at 1, 3, and 6 d using trypan blue exclusion. After 6 d of treatment with HQ (FIG. 7), 100% cytotoxicity towards melanocytes was observed at 100 µM, a concentration significantly lower than its $IC_{50}$. Even at 30 µM, HQ induced 60±2% and 70±3% cell death in fibroblasts and melanocytes, respectively. On the other hand, up to 300 µM P16-18 did not result in significant cell death, although treatment with 1-3 mM induced a 5-10% reduction in viability of both cell types. For keratinocytes, incubation for 6 d with 300 µM HQ resulted in 42±3% cell death, whereas an identical concentration of P16-18 induced less than 2.5% cell death. At 3 mM HQ, the rate of cell death was at 77±4%, compared to less than 10% for P16-18 (FIG. 7).

The MTT cell viability and proliferation assay showed very high toxicity for HQ towards primary human melanocytes, keratinocytes and fibroblasts after 72 h of incubation (FIG. 6), whereas minimal toxicity (<10%) was observed for the octapeptides at ≤3 mM. To better simulate the chronic use pattern of skin lightening products, cell viability was assessed after 6 d of treatment with varying doses of HQ or octapeptides. HQ was found to induce 100% cell death at a low concentration of 100 µM (FIG. 7). Melanocytes were found to be more sensitive to HQ than fibroblasts and keratinocytes. On the other hand, the octapeptides demonstrated limited toxicity towards all 3 cell types.

The above data support previous findings suggesting that the effect of HQ on pigmentation and melanogenesis is via degradation of melanosomes, and destruction of melanocytes (Ennes, S., Paschoalick, R., and Alchorne, M. M. D. A. (2000) *Journal of Dermatological Treatment* 11, 173-179; Penney, K. B., Smith, C. J., and Allen, J. C. (1984) *J Invest Dermatol* 82, 308-310). Furthermore, our study of HQ toxicity towards melanocytes, keratinocytes and fibroblasts, all key components of skin, showed that the ratio of 50% cytotoxic concentration to $IC_{50}$ is significantly less than one. For example, 20 µM HQ produced 50±3% melanocyte cell death after 6 days, and that concentration is 28-fold less than the $IC_{50}$. An ideal therapeutic agent should have a ratio that is higher than two to be considered safe for long-term use in humans. The oligopeptides did show potency well below the 50% cytotoxic dose with only 11% cytotoxicity at 3 mM versus $IC_{50}$ values of 238, 398, and 282 M for P16-18, respectively. This translates to a minimum ratio of ~8-12, although it is likely to be much higher since only 11% toxicity was observed at the highest dose tested.

P16-18 are not limited by the presence of a cysteine residue. Moreover, P15, a hexapeptide containing 2 cysteine residues, showed weak inhibition of tyrosinase, suggesting that cysteine was dispensable. The above data also suggest that arginine residues likely contribute more towards enzyme binding than inhibition. The novel octapeptides showed limited toxicity at therapeutically relevant concentrations, making them safer than HQ, which is known to derive its primary skin lightening activity via its cytotoxic effects. Although melanocyte toxicity may reduce skin pigmentation, it also results in permanent loss of pigmentation, inducing an undesirable confetti-like appearance. Moreover, the shorter chain length (8 amino acids) of P16-18 provides the potential advantage of lower cost, reduced allergenicity, and increased cellular penetration. In conclusion, the above findings suggest that oligopeptides P16-18 are ideal therapeutic candidates for cutaneous hyper-pigmentation disorders due to their potent inhibitory activity against tyrosinase and relative absence of melanocyte and fibroblast toxicity.

Other assays may be used in testing the present peptides. One may further screen for inhibitors of melanogenesis using assays for tyrosinase activity as described in US PGPUB 2004/0175767 by Orlow, et al., published Sep. 9, 2004, entitled "Methods and compositions that affect melanogenesis." As described there, one may cause tyrosinase to be secreted into a cellular medium for testing. Wild-type melanogenic cells grown in vitro culture will synthesize melanin inside of melanosomes as they do in vivo. In these cultured cells, tyrosinase is found predominantly in the melanosomal membrane, although some tyrosinase is also secreted. The tyrosinase that is found in the melanosomal membrane is held in place by a C-terminal transmembrane domain and has its active site disposed toward the melanosomal lumen. By contrast, in melanogenic cells inhibited for melanogenesis through either a mutation in P protein or a compound that inhibits P protein function, tyrosinase will be mislocalized. A significantly greater fraction of the cells' tyrosinase is secreted from the cells into the growth or incubation medium. Additionally, the secreted tyrosinase polypeptide will be shorter than that found in wild-type cells because it lacks its C-terminal membrane anchor. The secreted tyrosinase, however, is enzymatically active in the growth or incubation medium where it can synthesize melanin from extracellular tyrosine. Consequently, tyrosine-containing growth or incubation media from melanogenic cells that have been inhibited for melanogenesis will turn dark. The higher the concentration of tyrosine in the medium, the darker the medium becomes, and the higher the concentration of tyrosinase in the medium, the faster the medium darkens. Because melanogenic cells that are not inhibited for melanogenesis secrete significantly less tyrosinase, the tyrosine-containing growth or incubation media in which they are cultured will not become as dark.

In Vivo Assay

The peptides that exhibit significant tyrosinase inhibition in vitro may be further tested for their skin-whitening activity in vivo.

In this assay, healthy male and female volunteers (20-50 year old) receive about 0.6 J ultraviolet irradiation at two different spots in their brachial area, 2.25 cm² each, once every day for 3 days, and an inhibitory peptide is applied on either irradiated spot 3 times every day over 24 days. Thereafter, the irradiated spot with the skin-whitening agent is compared with control to estimate the degree of melanogenic suppression, i.e., skin-whitening effect.

The skin-whitening agent for such an assay may be prepared by mixing 10 parts by weight of ethanol and 0.18 parts by weight of methyl p-hydroxybenzoate together with either 0 (control), 4, 10, 16 or 40 parts by weight of 50 w/w % of either active peptide or a derivative adjusting the mixture to pH 5.5 with 10 w/w aqueous citric acid solution, and pouring refined water to the mixture to give a total amount of 100 parts by weight.

The concentration of peptide in the skin-whitening agent is therefore 0 w/w % (control), 2 w/w %, 5 w/w %, 8 w/w % or 20 w/w %.

The skin-whitening agent is applied by first soaking it in gauze, then attaching the gauze over an irradiated spot in accordance with the occlusive dressing technique.

Skin-whitening effect is determined by comparing the treated spot with control for melanogenic suppression, i.e., skin-whitening effect; grading the skin-whitening effect into either "superior", "not changed" or "inferior"; and numerating the volunteers answering "superior" (20 volunteers in each group).

Unlike the previous octapeptide (P3) (Abu Ubeid, A., Zhao, L., Wang, Y., and Hantash, B. M. (2009) *J Invest Dermatol* 129, 2242-2249) designed, P16-18 (SEQ ID NO: 2 and 3 respectively) are not limited by the presence of a cysteine residue. Furthermore, P16-18 show limited toxicity at therapeutically relevant concentrations, making them superior to both our previously designed tripeptide (P5) (Abu Ubeid, A., Zhao, L., Wang, Y., and Hantash, B. M. (2009) *J Invest Dermatol* 129, 2242-2249) as well as HQ, which is known to derive its primary skin lightening activity via its cytotoxic effects. Although melanocyte toxicity may reduce skin pigmentation, it also results in permanent loss of pigmentation (Fisher, A. A. (1983) *Cutis* 31, 240-244, 250; McGregor, D. (2007) *Crit Rev Toxicol* 37, 887-914), inducing a vitiligo-like appearance incapable of responding to ultraviolet light via normal tanning. This is clearly not a desirable outcome. In addition, P16-18 are all 2 amino acids shorter than a previously disclosed decapeptide (P4) (Abu Ubeid, A., Zhao, L., Wang, Y., and Hantash, B. M. (2009) *J Invest Dermatol* 129, 2242-2249), providing the potential advantage of lower cost, reduced allergenicity, and increased cellular penetration. In conclusion, the present findings suggest that peptides P16-18 SEQ ID NO: 1, 2 and 3 respectively) are ideal candidates as tyrosinase inhibitors due to their potent inhibitory activity against tyrosinase and relative absence of melanocyte and fibroblast toxicity, unlike HQ which was shown to derive its primary skin lightening activity via its cytotoxic effects.

CONCLUSION

The above specific description is meant to exemplify and illustrate the invention and should not be seen as limiting the scope of the invention. Any patents or publications mentioned in this specification are indicative of levels of those skilled in the art to which the patent or publication pertains as of its date and are intended to convey details of the invention which may not be explicitly set out but which would be understood by workers in the field. Such patents or publications are hereby incorporated by reference to the same extent as if each was specifically and individually incorporated by reference, as needed for the purpose of describing and enabling the method or material referred to.

What is claimed is:

1. A formulation comprising:
a peptide which inhibits tyrosinase, according to one of formulas (a) and (b):
(a) $X^1 X^2$ R Y W Y Y $X^8$ (SEQ ID NO: 16) and
(b) $X^1 X^2$ Y W Y W $X_7 X^8$ (SEQ ID NO: 17),
where $X^1, X^2, X^7$ and $X^8$ are each independently one of R, Y, and missing,
where at least one amino acid in the peptide is in a right-handed (D) configuration; and
an emulsion carrier comprising oil and water.

2. A formulation according to claim 1 wherein $X^1, X^2, X^7$ and $X^8$ are each independently Y or R.

3. A formulation according to claim 2 wherein in formula (a), $X^1, X^2$, and $X^8$ are R; and in formula (b) $X^1, X^2, X^7$, and $X^8$ are R.

4. A formulation according to claim 1 wherein $X^1$ and $X^8$ are missing in each of said formula a) and (b).

5. A formulation according to claim 1 wherein $X^1, X^2$, and $X^8$ are missing in each of said formula (a) and (b).

6. A formulation according to claim 1 wherein $X^1$ is R in each of said formula (a) and (b).

7. A formulation according to claim 1 formula (a) wherein $X^1, X^2$, and $X^8$ are R or missing.

8. A formulation according to claim 7 wherein $X^1, X^2$, and $X^8$ are R.

9. A formulation according to claim 1 formula (b) wherein $X^1$ and $X^2$ are both R.

10. A formulation according to claim 9 wherein $X^7$ and $X^8$ are both R.

11. A formulation according to claim 1 formula (b) wherein $X^1, X^2, X^7$, and $X^8$ is R or missing.

12. A formulation according to claim 1 formula (a) or (b) wherein at least one of the following pairs is missing: $X^1$ and $X^2$; $X^1$ and $X^8$; and $X^7$ and $X^8$.

13. A dermatologically acceptable formulation comprising a secondary treatment agent, a peptide as defined in claim 1, and a suitable carrier.

14. A dermatological formulation comprising a peptide selected from the group consisting of RRWWRRYY (SEQ ID NO: 1), RRWWRR (SEQ ID NO: 7), RWWRRY (SEQ ID NO: 9), RRRYWYYR (SEQ ID NO: 2), RRYWYY(SEQ ID NO: 10), RYWYYR(SEQ ID NO: 11), RRYWYWRR(SEQ ID NO: 3), RRYWYW (SEQ ID NO: 12), RYWYWR (SEQ ID NO: 13) and YWYWRR (SEQ ID NO: 14), where at least one amino acid in the peptide is in a right-handed (D) configuration, with the proviso that one amino acid substitution is permitted in a sequence in said group, wherein W may be Y or F; Y may be W or F; or R may be K, mixed with a suitable carrier, wherein the carrier has a viscosity ranging from 0.01 centistokes to 50 centistokes.

15. The formulation of claim 14 which is substantially free of HQ.

16. The formulation of claim 14 further comprising a material selected from: hydrating formulations, antioxidant formulations, and free radical scavengers.

17. The formulation of claim 14 wherein the peptide is contained in liposomes.

18. The formulation of claim 14 wherein said peptide is present in a concentration of between 0.1 and 0.4 grams per ounce of formulation.

19. A formulation for inhibiting tyrosinase comprising:
a peptide, according to the formula:
$X^1$ R W W R $X^6$ $X^7$ $X^8$ (SEQ ID NO: 15),
where $X^1$, $X^6$, $X^7$ and $X^8$ are each independently one of R, Y, and missing, and where at least one amino acid in the peptide is in a right-handed (D) configuration; and
a physiologically suitable carrier, wherein the formulation has a pH of 6.8 to 8.0 while the formulation is at a temperature of approximately 17 degrees Celsius.

20. The formulation according to claim 19 wherein $X^7$ is Y or missing.

21. The formulation according to claim 19 wherein $X^8$ is Y or missing.

22. The formulation according to claim 19 wherein the carrier is an emulsion carrier and the carrier includes an anti-foaming agent.

23. The formulation according to claim 19 wherein the formulation is a cream formulation and the peptide is present in a peptide concentration ranging from 0.47 millimolar to 0.8 millimolar.

24. A method of inhibiting tyrosinase comprising:
administering to skin a peptide according to one of formulas (a), (b), and (c):
(a) $X^1$ R W W R $X^6$ $X^7$ $X^8$ (SEQ ID NO: 15),
(b) $X^1$ $X^2$ R Y W Y Y $X^8$ (SEQ ID NO: 16), and
(c) $X^1$ $X^2$Y W Y W $X^7$ $X^8$ (SEQ ID NO: 17),
where $X^1$, $X^2$, $X^6$, $X^7$ and $X^8$ are each independently one of R, Y, and missing, and where at least one amino acid in the peptide is in a right-handed (D) configuration.

* * * * *

```
SEQUENCE LISTING

<160> NUMBER OF SEQ ID NOS: 17

<210> SEQ ID NO 1
<211> LENGTH: 8
<212> TYPE: PRT
<213> ORGANISM: artificial
<220> FEATURE:
<223> OTHER INFORMATION: synthetic peptide

<400> SEQUENCE: 1

Arg Arg Trp Trp Arg Arg Tyr Tyr
1               5

<210> SEQ ID NO 2
<211> LENGTH: 8
<212> TYPE: PRT
<213> ORGANISM: artificial
<220> FEATURE:
<223> OTHER INFORMATION: synthetic peptide

<400> SEQUENCE: 2

Arg Arg Arg Tyr Trp Tyr Tyr Arg
1               5

<210> SEQ ID NO 3
<211> LENGTH: 8
<212> TYPE: PRT
<213> ORGANISM: artificial
<220> FEATURE:
<223> OTHER INFORMATION: synthetic peptide

<400> SEQUENCE: 3

Arg Arg Tyr Trp Tyr Trp Arg Arg
1               5

<210> SEQ ID NO 4
<211> LENGTH: 5
<212> TYPE: PRT
<213> ORGANISM: artificial
<220> FEATURE:
<223> OTHER INFORMATION: synthetic peptide
```

```
<400> SEQUENCE: 4

Arg Arg Val Ala Leu
1               5

<210> SEQ ID NO 5
<211> LENGTH: 6
<212> TYPE: PRT
<213> ORGANISM: artificial
<220> FEATURE:
<223> OTHER INFORMATION: synthetic peptide

<400> SEQUENCE: 5

Arg Arg Phe Val Leu Leu
1               5

<210> SEQ ID NO 6
<211> LENGTH: 6
<212> TYPE: PRT
<213> ORGANISM: artificial
<220> FEATURE:
<223> OTHER INFORMATION: synthetic peptide

<400> SEQUENCE: 6

Arg Arg Phe Val Cys Cys
1               5

<210> SEQ ID NO 7
<211> LENGTH: 6
<212> TYPE: PRT
<213> ORGANISM: artificial
<220> FEATURE:
<223> OTHER INFORMATION: synthetic peptide

<400> SEQUENCE: 7

Arg Arg Trp Trp Arg Arg
1               5

<210> SEQ ID NO 8
<211> LENGTH: 4
<212> TYPE: PRT
<213> ORGANISM: artificial
<220> FEATURE:
<223> OTHER INFORMATION: synthetic peptide

<400> SEQUENCE: 8

Arg Trp Trp Arg
1

<210> SEQ ID NO 9
<211> LENGTH: 6
<212> TYPE: PRT
<213> ORGANISM: artificial
<220> FEATURE:
<223> OTHER INFORMATION: synthetic peptide

<400> SEQUENCE: 9

Arg Trp Trp Arg Arg Tyr
1               5

<210> SEQ ID NO 10
<211> LENGTH: 6
<212> TYPE: PRT
<213> ORGANISM: artificial
<220> FEATURE:
<223> OTHER INFORMATION: synthetic peptide

<400> SEQUENCE: 10
```

```
Arg Arg Tyr Trp Tyr Tyr
1               5

<210> SEQ ID NO 11
<211> LENGTH: 6
<212> TYPE: PRT
<213> ORGANISM: artificial
<220> FEATURE:
<223> OTHER INFORMATION: synthetic peptide

<400> SEQUENCE: 11

Arg Tyr Trp Tyr Tyr Arg
1               5

<210> SEQ ID NO 12
<211> LENGTH: 6
<212> TYPE: PRT
<213> ORGANISM: artificial
<220> FEATURE:
<223> OTHER INFORMATION: synthetic peptide

<400> SEQUENCE: 12

Arg Arg Tyr Trp Tyr Trp
1               5

<210> SEQ ID NO 13
<211> LENGTH: 6
<212> TYPE: PRT
<213> ORGANISM: artificial
<220> FEATURE:
<223> OTHER INFORMATION: synthetic peptide

<400> SEQUENCE: 13

Arg Tyr Trp Tyr Trp Arg
1               5

<210> SEQ ID NO 14
<211> LENGTH: 6
<212> TYPE: PRT
<213> ORGANISM: artificial
<220> FEATURE:
<223> OTHER INFORMATION: synthetic peptide

<400> SEQUENCE: 14

Tyr Trp Tyr Trp Arg Arg
1               5

<210> SEQ ID NO 15
<211> LENGTH: 8
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid

<400> SEQUENCE: 15

Xaa Arg Trp Trp Arg Xaa Xaa Xaa
1               5

<210> SEQ ID NO 16
```

```
<211> LENGTH: 8
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 16

Xaa Xaa Arg Tyr Trp Tyr Tyr Xaa
1               5

<210> SEQ ID NO 17
<211> LENGTH: 8
<212> TYPE: PRT
<213> ORGANISM: artificial
<220> FEATURE:
<223> OTHER INFORMATION: synthetic peptide
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 17

Xaa Xaa Tyr Trp Tyr Trp Xaa Xaa
1               5
```